(12) United States Patent  (10) Patent No.: US 8,877,207 B2
Cimini et al.  (45) Date of Patent: Nov. 4, 2014

(54) NANOPARTICLES OF CERIUM OXIDE TARGETED TO AN AMYLOID-BETA ANTIGEN OF ALZHEIMER'S DISEASE AND ASSOCIATED METHODS

(75) Inventors: Annamaria Cimini, L'Aquila (IT); Barbara D'Angelo, L'Aquila (IT); Soumen Das, Orlando, FL (US); Sudipta Seal, Orlando, FL (US)

(73) Assignees: University of Central Florida Research Foundation, Inc., Orlando, FL (US); University of l'Aquila, L'Aquila, Abruzzo (IT)

( * ) Notice: Subject to any disclaimer, the term of this patent is extended or adjusted under 35 U.S.C. 154(b) by 0 days.

(21) Appl. No.: 13/184,660

(22) Filed: Jul. 18, 2011

(65) Prior Publication Data

US 2012/0070500 A1  Mar. 22, 2012

Related U.S. Application Data

(60) Provisional application No. 61/383,773, filed on Sep. 17, 2010.

(51) Int. Cl.
| | |
|---|---|
| *A61K 9/14* | (2006.01) |
| *A61K 39/385* | (2006.01) |
| *A61K 38/00* | (2006.01) |
| *A61K 47/48* | (2006.01) |
| *B82Y 5/00* | (2011.01) |

(52) U.S. Cl.
CPC ..... *A61K 47/48907* (2013.01); *A61K 47/48538* (2013.01); *A61K 47/48861* (2013.01); *B82Y 5/00* (2013.01)
USPC .... 424/194.1; 424/489; 424/9.32; 424/193.1; 514/17.7; 514/17.8

(58) Field of Classification Search
CPC .................. A61K 47/48907; A61K 47/48538; A61K 47/48861; B82Y 5/00
See application file for complete search history.

(56) References Cited

U.S. PATENT DOCUMENTS

| | | | |
|---|---|---|---|
| 5,089,860 | A | 2/1992 | Deppe et al. |
| 5,411,647 | A | 5/1995 | Johnson et al. |

(Continued)

FOREIGN PATENT DOCUMENTS

| | | |
|---|---|---|
| WO | WO 99/15891 | 4/1999 |
| WO | WO 03/059263 A2 | 7/2003 |

(Continued)

OTHER PUBLICATIONS

Geylis and Steinitz "Immunotherapy of Alzheimer's disease (AD): From murine models to anti-amyloid beta (A.beta.) human monoclonal antibodies" Autoimmunity Reviews, Aug. 1, 2005. vol. 5 p. 33-39.*

(Continued)

*Primary Examiner* — Gregory S Emch
*Assistant Examiner* — Adam M Weidner
(74) *Attorney, Agent, or Firm* — Timothy H. Van Dyke; Beusse, Wolter, Sanks & Maire, P.A.

(57) ABSTRACT

Disclosed is a composition immunologically targeted to Alzheimer's disease (AD), the composition containing amine functionalized nanoparticles of Cerium oxide coated with polyethylene glycol and bearing an antibody specific for an amyloid-beta antigen associated with AD. The invention also includes a medication manufactured with the targeted nanoceria particles and methods of treatment by administering the targeted nanoceria particles to patients in need thereof.

11 Claims, 12 Drawing Sheets

(56) References Cited

U.S. PATENT DOCUMENTS

| | | | |
|---|---|---|---|
| 5,486,359 | A | 1/1996 | Caplan et al. |
| 5,910,311 | A | 6/1999 | Boussourira |
| 5,961,993 | A | 10/1999 | Boussourira |
| 6,042,714 | A | 3/2000 | Lin et al. |
| 6,103,247 | A | 8/2000 | Boussourira et al. |
| 6,139,985 | A | 10/2000 | Borglum et al. |
| 6,316,012 | B1 | 11/2001 | N'Guyen |
| 6,327,074 | B1 | 12/2001 | Bass et al. |
| 6,368,577 | B1 | 4/2002 | Kropf et al. |
| 6,406,685 | B1 | 6/2002 | Philippe |
| 6,468,551 | B1 | 10/2002 | Diec |
| 6,497,863 | B1 | 12/2002 | Wachter |
| 6,497,865 | B1 | 12/2002 | Griesbach |
| 6,501,590 | B2 | 12/2002 | Bass et al. |
| 6,592,746 | B1 | 7/2003 | Schmid-Schoenbein et al. |
| 6,654,161 | B2 | 11/2003 | Bass et al. |
| 6,844,387 | B2 | 1/2005 | Bass et al. |
| 6,890,896 | B1 | 5/2005 | Shashoua |
| 7,005,504 | B2 | 2/2006 | Hsei et al. |
| 7,075,707 | B1 | 7/2006 | Rapaport et al. |
| 7,141,227 | B2 | 11/2006 | Chan |
| 7,270,813 | B2 | 9/2007 | Shimp et al. |
| 7,347,987 | B2 | 3/2008 | McGinnis et al. |
| 7,431,758 | B2 | 10/2008 | Ota et al. |
| 7,442,686 | B2 | 10/2008 | Lasko et al. |
| 7,471,706 | B2 | 12/2008 | Bass et al. |
| 7,504,356 | B1 | 3/2009 | Self et al. |
| 7,507,480 | B2 | 3/2009 | Sugaya |
| 7,534,453 | B1 | 5/2009 | Zigalizknski |
| 7,563,459 | B2 | 7/2009 | Phillips et al. |
| 7,642,250 | B2 | 1/2010 | Williams |
| 7,687,505 | B2 | 3/2010 | Sugaya |
| 7,725,802 | B2 | 5/2010 | Eroz et al. |
| 7,772,375 | B2 | 8/2010 | Greferath et al. |
| 7,888,119 | B2 | 2/2011 | Sugaya et al. |
| 7,899,093 | B1 | 3/2011 | Bass et al. |
| 7,906,147 | B2 | 3/2011 | Hainfield et al. |
| 7,914,617 | B2 | 3/2011 | Yadav |
| 8,080,420 | B2 | 12/2011 | Sugaya |
| 8,097,270 | B2 | 1/2012 | Ketelson et al. |
| 8,172,901 | B2 | 5/2012 | Altman et al. |
| 2003/0050709 | A1 | 3/2003 | Noth et al. |
| 2003/0187077 | A1 | 10/2003 | Chane-Ching |
| 2004/0062753 | A1 | 4/2004 | Rezania et al. |
| 2005/0036928 | A1 | 2/2005 | Katusic et al. |
| 2005/0159820 | A1 | 7/2005 | Yoshikawa et al. |
| 2005/0164377 | A1 | 7/2005 | Miyabayashi et al. |
| 2005/0171192 | A1 | 8/2005 | Gehlsen |
| 2006/0110440 | A1 | 5/2006 | Sugaya |
| 2006/0280729 | A1 | 12/2006 | Mistry |
| 2007/0003621 | A1 | 1/2007 | Nagia et al. |
| 2007/0166311 | A1 | 7/2007 | Greferath et al. |
| 2008/0089836 | A1 | 4/2008 | Hainfield et al. |
| 2009/0087493 | A1 | 4/2009 | Dai et al. |
| 2009/0098574 | A1 | 4/2009 | Brisson et al. |
| 2010/0151000 | A1 | 6/2010 | Thomas et al. |

FOREIGN PATENT DOCUMENTS

| | | |
|---|---|---|
| WO | WO 2006/118954 A2 | 11/2006 |
| WO | WO 2007/002662 A2 | 1/2007 |
| WO | WO 2008/064357 A2 | 5/2008 |
| WO | WO 2009/132277 A1 | 10/2009 |

OTHER PUBLICATIONS

Das, Swanand, Bhargava, Kang, Riedel, Seal, and Hickman. "Autocatalytic Ceria Nanoparticles Offer Neuroprotection to Adult Rat Spinal Cord Neurons" Biomaterials epub: Jan. 12, 2007. vol. 28(10) p. 1918-1925.*

Karakoti et al. (2008) Nanoceria as Antioxidant: Synthesis and Biomedical Applications. JOM (1989). 60(3):33-37.*

Patil et al., Surface-Derived nanoceria with Human Carbonic Anhydrase II Inhibitors and Fluorphores: A Potential Drug Delivery Device. J. Phys. Chem. C., 2007, vol. 111, No. 24, pp. 8437-8442.

Patil et al. Synthesis of nanocrystalline ceria particles for high temperature oxidation resistant coating. Journal of Nanoparticle Research, 2002, vol. 4: pp. 433-438.

Jin et al. Nanoparticle-Mediated Drug Delivery and Gene Therapy. Biotechnol. Prog., 2007, vol. 23, pp. 32-41.

Eck et al. PEGylated Gold Nanoparticles Conjugated to Monoclonal F19 Antibodies as Targeted Labeling Agents for Human Pancreatic Carcinoma Tissue. ACS Nano, 2008, vol. 2 (11), pp. 2263-2272.

Nafee. Dissertation entitled Cationically-modified nanoparticles for the pulmonary delivery of the telomerase inhibitor 2'-O-Methyl RNA for the treatment of lung cancer. Disseration zur Erlangung des Grades des Doktors der, Naturwissenschaften der Naturwissenschaftilch-Technischen Fakul't III Chemie, Pharmazie, Bio-und Werstoffwissenschaften der Universit des Saarlandes, 2008.

Nazem et al. Nanotechnology for Alzheimer's disease detection and treatment. Insciences J. 2011, vol. 1(4), pp. 169-193; published Oct. 4, 2011.

Oliver et al. Synthesis of Pegylated Immunonanoparticles. Pharmaceutical Research, Aug. 2002, vol. 19, No. 8, pp. 1137-1143.

Otsuka et al. PEGylated nanoparticles for biological and pharmaceutical applications. Advanced Drug Delivery Reviews, 2003, vol. 55, pp. 403-419.

Qi et al. Redispersible Hybrid Nanopowders; Cerium Oxide Nanoparticle complexes with Phosphonated-PEG Oligomers. ACS Nano, 2008, vol. 2 (5), pp. 879-888.

Sokolov et al. Real-Time Vital Optical Imaging of Precancer Using Anti-Epidermal Growth Factor Receptor Antibodies Conjugated to Gold Nanoparticles. Cancer REs., 2003, vol. 63:1999, 2004.

Suh et al. Multifunctional nanosystems at the interface of physical and life sciences. Physicaplus, Apr. 15, 1010, Issue No. 13 available online at <http://physicaplus.org.il/zope/home/en/1224031001/multi_nano_en>.

Suzuki et al. Preparation and characteristics of magnetitelabelled antibody with the use of poly(ethylene glycol) derivatives. Biotechnol. Appl. Biochem., 1995, vol. 21, pp. 335-345.

PCT International Search Report and the Written Opinion of the International Searching Authority.

Sokolov, et al. , "Real-time vital optical imaging of precancer using anti-epidermal growth factor receptor antibodies conjugated to gold nanoparticles." Cancer Res. 2003, vol. 63:1999, 2004.

Niu, J., et al. "Cardioprotective effects of cerium oxide nanoparticles in a transgenic murine model of cardiomyopathy," Cardiovas. Res. Nov. 30, 2006, vol. 73, No. 3, pp. 549-559.

Qureshi, M.A., et al. "Increased exhaled nitric oxide following autologous peripheral hemotopietic stem cell transplantation; a potential marker of idopathic pneumonia syndrome," Chest, Jan. 2004, vol. 125, No. 1, pp. 281-287.

Ohgushi, et al., "Stem Cell Technology and Bioceramics: From Cell to Gene Engineering", J. Biomed. Mat. Res. 48:913-927; 1999.

Dal Maschio, et al., "Influence of Ce3+/Ce 4+ ratio on phase stability and residual stress field in ceria-yttria stabilized zirconia plasma-sprayed coatings", J. Mat. Sci. 27: 5591-5596; 1992.

Ramsfjell, et al., "Distinct Requirements for Optimal Growth and In Vitro Expansion of Human CD341CD382 Bone Marrow Long-Term Culture-Initiating Cells (LTC-IC), Extended LTC-IC, and Murine In Vivo Long-Term Reconstituting Stem Cells", Blood 99: 4093-4102; 1999.

Devasenpathi, et al., "Forming near net shape free-standing components by plasma spraying", Mat. Let. 57: 882-886; 2002.

Imamura, et al. "Drusen, choridal neovascularization and retinal pigment epithelium dysfunction in SOD1-deficient mice: A model of age-related macular degeneration," PNAS, vol. 103, No. 30; 11282-11287 (Jul. 25, 2006).

Hollyfield, et al. "Oxidative damage-induced inflammation initiates age-related macular degeneration," Nature Medicine, vol. 14, pp. 194-198 (2008).

Birch, et al. Age-related macular degeneration: a target for nanotechnology derived medicines. International Journal of Nanomedicine, 2007, 2(1), 65-77.

Maulik, N. Reactive oxygen species drives myocardial angiogenesis? Antioxidants & Redox Signaling, 2006, 8 (11-12) 2161-2168.

(56) References Cited

OTHER PUBLICATIONS

Kuchibhatla et al., "Hierarchical assembly of inorganic nanostructure building blocks to octahedral superstructures a true template-free self-assembly", Nanotechnology, 2007, vol. 18, pp. 1-4.
Ohia, et al. "Pharmacological consequences of oxidative stress in ocular tissues," Mutation Research, 2005, 579, 22-36.
Liu, et al. "Subtype lesions of neovascular age-related macular degeneration in Chinese paitents," Braefe's Arch Clin Exp Opthalmol, 2007, 245, 1441-1445.
Silva. "Seeing the benefits of ceria," Nature Nanotechnology, 2006, 1, 92-94.
Hahn, et al. "Maculas affected by Age-Related Macular Degeneration Contain Increased Chelatable Iron in the Retinal Pigment Epithelium and Bruch's Membrane,"Arch. Opthalmol. 2003, 121, 1099-1105.
Haywood, et al. "Inflammation and Angiogenesis in Osteoarthritis," Arthritis & Rheumatism, 2003, 48 (8), 2173-2177.
Chen, et al. Rare Earth Nanoparticles Prevent Retinal Degeneration Induced by Intracellular Peroxides: Nature Nano Technology, 1(2) 142-148 (2006).
Moongkarndi, et al. "Antiproliferation, antioxidation and induction of apoptosis by *Garcinia mangostana* (mangosteen) on SKBR3 human breast cancer cell line," J. of Ethno-Pharmacology, vol. 90, (2004) pp. 161-166.
Margrain, et al. "Do blue light filters confer protection against age-related macular degeneration?", Progress in Retinal and Eye Research, vol. 23 (2004) pp. 523-531.
Bailey, et al. "Cerium Oxide Nanoparticles Extend Cell Longevity and Act as Free Radical Scavengers," online (retrieved on Apr. 24, 2006) from: http://www.med.miami.edu/mnbws/Rzigalinski11.html.
Tsai, Ming-Shyong. "The Study of the synthesis of nano-grade cerium oxide powder," Materials Letters 58, 2270-2274 (2004).
Rzigalinski, Beverly Ann, et al. "Cerium Oxide nanoparticles increase the lifespan of cultured brain cells and protect against free radical mechanical trauma" FASEB Journal, vol. 17 No. 4-5, p. Abstract No. 377.24 URL, XP008095016 & FASEB Meeting on Experimental Biology: Translating the Genome, San Diego, CA, USA, Apr. 11-15, 2003 ISSN: 0892-6638 *Abstract*.
Cook, et al. "Neuronal Damage induced by polychlorinated biphenyls is partically reversed by cerium oxide nanoparticles" [online] vol. 2003, 2003, XP008095032 Retrieved from the internet: URL http://sfn.scholarone.com/itin2003/main.htm]?new_page_id=126&abstract_id=14513&p_num=669.13&is_tech=0> [retrieved on Aug. 5, 2008] *abstract*.
Tusnekawa, S., et al. "Lattice relaxation of monosize Ce02-x nanocrystalline particles" Applied Surface Science Elsevier Netherlands, vol. 152, No. 1-2, Nov. 1999, pp. 53-56.
Hooper, Claire, Y., et al. "New treatment in age-related macular degeneration" Clinical & Experimental Opthalmology, Oct. 2003, pp. 376-391.
Qi, et al. "Redispersible Hybrid Nanopowders; Cerium Oxide Nanoparticle complexes with Phosphonated-PEG Oligomers," ACS Nano, 2008, vol. 2(5), pp. 879-888.
Otsuka, et al. "PEGylated nanoparticles for biological and pharmaceutical applications," Advanced Drug Delivery Reviews, 2003, vol. 55, pp. 403-419.
Olivier, et al. "Synthesis of pegylated immunonanoparticles." Pharmaceutical Research, Aug. 2002, vol. 19, No. 8, pp. 1137-1143.
Xijuan, et al. "Size-dependent optical properties of nanocrystalline Ce02:Er obtained by combustion synthesis," Sep. 24, 2001, Phys. Chem. Chem Phys., vol. 3, pp. 5266-5269.
Guo, "Green and red upconversion luminescence in Ce02:Er3+ powders produced by 785 nm laser," Jounral of Solid State Chemistry 180, p. 127-131, 2007.
Perez, J. M., et al. "Synthesis of Biocompatible Dextran-Coated Nanoceria with pH-Dependent Antioxidant Properties," Small, vol. 4 No. 5, 2008, pp. 552-556.

Pirmohamed, et al. "Nanoceria exhibit redox state-dependent catalase mimetic activity," Chem. Comm, 2010, 46, pp. 2736-2738.
Nazem, et al. "Nanotechnology for Alzheimer's disease detection and treatment." Insciences J., 2011, vol. 1(4), pp. 169-193.
Karakoti, et al. "Direct Synthesis of Nanoceria in Aqueous Polyhydroxyl Solutions." J. Phys. Chem. C, vol. 111, No. 46, 2007, pp. 17232-17240.
Tarnuzzer, et al. "Vacancy Engineered Ceria Nanostructures for Protection from Radiation-Induced Cellular Damage," Nano Lett, vol. 4, No. 12, pp. 2573-2577.
Heckert, et al. "The role of cerium redox state in the SOD mimetic activity of nanoceria," Biomaterials, 29, 2008, pp. 2705-2709.
Schubert, et al. "Cerium and yttrium oxide nanoparticles are neuroprotective," Feb. 2006, Biochemical and Biophysical Research Communications, 342, p. 86-91.
Zhang, et al. Cerium oxide nanoparticles: size selective formation and structure analysis, Jan. 2002, Applied Physics Letters, vol. 81, No. 1, p. 127-129.
Patil, et al. "Surface-derived nanoceria with human carbonic anhydrase II inhibitors and flourphores: a potential drug delivery device." J. Phys. Chem. C., 2007, vol. 111, No. 24, pp. 8437-8442.
Patil, et al. "Synthesis of nanocrystalline ceria particles for high temperature oxidation resistant coating," Journal of Nanoparticle Research, 2002, vol. 4: pp. 433-438.
Jin, et al. "Nanopartical-mediated drug delivery and gene therapy," Biotechnol. Prog, 2007, vol. 23, pp. 32-41.
Eck, et al. "PEGylated gold nanoparticles conjugated to monoclonal F19 antibodies as targeted labeling agents for human pancreatic carcinoma tissue," ACS Nano, 2008, vol. 2(11) pp. 2263-2272.
Suh et al., "Multifunctional nanosystems at the interface of physical and life sciences", Nano Today, 2009, vol. 4, pp. 27-36.
Suzuki et al., "Preparation and characteristics of magnetite labelled antibody with the use of poly(ethylene glycol) derivatives", Biotechnol. Appl. Biochem., 1995, vol. 21, pp. 335-345.
Monte et al., "Inhibition of lymphocyte induced angiogenesis by free radical scavengers", Free Radic Biol Med, 1994, vol. 17, pp. 259-266.
PCT/US2011/0044329; PCT International Search Report and Written Opinion, 2011 (1 page).
Harman D. "The Free Radical Theory of Aging." Antioxid Redox Sign 2003; vol. 5: pp. 557-561.
Halliwell B. "Oxidative stress and neurodegeneration: where are we now?" J Neurochem 2006; vol. 97: pp. 1634-1658.
Howes RM. "The Free Radical Fantasy." Ann New York Acad 2 o Scis, 2006; vol. 1067: pp. 22-26.
Warner OS, et al, "Oxidants, antioxidants and the ischemic brain." J Exp Bioi, 2004; vol. 207: pp. 3221-3231.
Inestrosa NC, et al. "Acetylcholinesterase Accelerates Assembly of Amyloid-[beta]-Peptides into Alzheimer's Fibrils: Possible Role of the Peripheral Site of the Enzyme Neuron" 1996; vol. 16: pp. 881-891.
Leker RR, et al. "Cerebral ischemia and trauma—different etiologies yet similar mechanisms: neuroprotective opportunities." Brain Research Reviews 2002; vol. 39: pp. 55-73.
Knott AB, et al. "Mitochondrial fragmentation in neurodegeneration." Nat Rev Neurosci 2008; vol. 9: pp. 505-518.
Korsvik C, et al. "Superoxide dismutase mimetic properties exhibited by vacancy engineered ceria nanoparticles." Chemi Commun, vol. 2007: pp. 1056-1058.
Santos MJ, et al. "Peroxisomal Proliferation Protects from -Amyloid Neurodegeneration." Journal of Biological Chemistry, 2005; vol. 280: pp. 41057-41068.
Aneggi E, et al. "Insights into the redox properties of ceria-based oxides and their implications in catalysis." J Alloys and Compounds 2006; vol. 408-412: pp. 1096-1102.
Naiki H, et al. "Kinetic analysis of amyloid fibril polymerization in vitro", Lab Invest, 1991; vol. 65: pp. 104-110.
Zhang F, et al. "Cerium oxidation state in ceria nanoparticles studied with X-ray photoelectron spectroscopy and absorption near edge spectroscopy." Surface Science, 2004; vol. 563: pp. 74-82.
Davis VT, et al. "Measurement of the Electron Affinity of Cerium." Phys Rev Lett, 2002; vol. 88.073003.

(56) References Cited

OTHER PUBLICATIONS

Karakoti A, et al. "Redox-active radical scavenging nanomaterials." Chem Soc Revs, 2010; vol. 39: pp. 4422-4432.

Varadarajan S, et al. "Different Mechanisms of Oxidative Stress and Neurotoxicity Alzheimer's A beta(1-42) and A beta(25-35)." Journal of the American Chemical Society, 2001; vol. 123: pp. 5625-5631.

White JA, et al. "Differential effects of oligomeric and fibrillar amyloid-[beta]1-42 on astrocyte-10 mediated inflammation." Neurobiology of Disease, 2005; vol. 18: pp. 459-465.

Celardo I, et al. "Cerium oxide nanoparticles: a promise for applications in therapy." J Exp Ther Oncol, 2011; vol. 9: pp. 47-51.

Celardo I, et al. "Pharmacological potential of cerium oxide nanoparticles." Nanoscale, 2011. [Epub ahead of print].

Hirst SM, et al. "Anti-inflammatory Properties of Cerium Oxide Nanoparticles." Small, 2009; vol. 5: pp. 2848-2856.

Alili L, al. et al "Combined cytotoxic and anti-invasive properties of redox-active nanoparticles in tumor-stroma interactions." Biomaterials, 2011; vol. 32: pp. 2918-2929.

Colon J, et al. "Cerium oxide nanoparticles protect gastrointestinal epithelium from radiation-induced damage by reduction of reactive oxygen species and upregulation of superoxide dismutase 2." Nanomedicine—UK2010; vol. 6: pp. 698-705.

Varghese K, et al. "Regeneration and characterization of adult mouse hippocampal neurons in a defined in vitro system." J Neurosci Meth, 2009; vol. 177: pp. 51-59.

D'Angelo B, et al. "Falone Set ai . . . Cerium Oxide Nanoparticles Trigger Neuronal Survival in a Human Alzheimer Disease Model by Modulating BDNF Pathway." Curr Nanosci, 2009; vol. 5: pp. 167-176.

Vincent A, et al. "Protonated Nanoparticle Surface Governing Ligand Tethering and Cellular Targeting." ACS Nano 2009; vol. 3:pp. 1203-1211.

Di Loreto S, et al. "PPARagonists trigger neuronal differentiation in the human neuroblastoma cell line SH-SY5Y." J Cell Physiol 2007; vol. 211: pp. 837-847 (2007).

D'Angelo B, et al. "Signal transduction pathways involved in pparB/5-induced neuronal differentiation." J Cell Physiol, Epub ahead of print] (2010).

Cimini A. Benedetti E, et al. "Expression of peroxisome proliferator-activated receptors (PPARs) and retinoic acid receptors (RXRs) in rat cortical neurons." Neuroscience, 2005; vol. 130: pp. 325-337.

Teng HK, et al. "ProBDNF Induces Neuronal Apoptosis via Activation of a Receptor Complex of p75NTR and Sortilin." The Journal of Neuroscience, 2005; vol. 25:pp. 5455-5463.

Das M. et al. "Auto-catalytic ceria nanoparticles offer neuroprotection to adult rat spinal cord neurons." Biomaterials, 2007; vol. 28: pp. 1918-1925.

Munoz et al. "Neurotoxicity of acetylcholinesterase amyloid betapeptide aggregates is dependent on the type of Abeta peptide and the AChE concentration present in the complexes." FEBS Letters, 1999; vol. 450: pp. 205-209.

Karakoti AS, et al. "Thevuthasan S & SealS. PEGylated Inorganic Nanoparticles." Angewandte Chemie International Edition, 2011; vol. 50: pp. 1980-1994.

Hsu CH, et al. "Preparation and Characterization of Novel Coenzyme Q10 Nanoparticle Engineered from Microemulsion Precursors AAPS" PharmSciTech, 2003; vol. 4: pp. E32.

Cui Z et al. "Topical immunization using nanoengineered genetic vaccines." Journal of Controlled Release, 2002; vol. 81: pp. 173-184.

Cui Z , et al. "Genetic Immunization Using Nanoparticles Engineered from Microemulsion Precursors." Pharmaceutical Research, 2002; vol. 19: pp. 939-946.

Lockman PR, et al. "Assessment of Baseline Blood-Brain Barrier Parameters in the Presence of Novel Nanoparticles." Pharmaceutical Research, 2003; vol. 20: pp. 705-713.

Dong et al., "Activation of glassy carbon electrodes by dispersed metal oxide particles", J. Electrochem Soc., 1984, pp. 813-819.

* cited by examiner

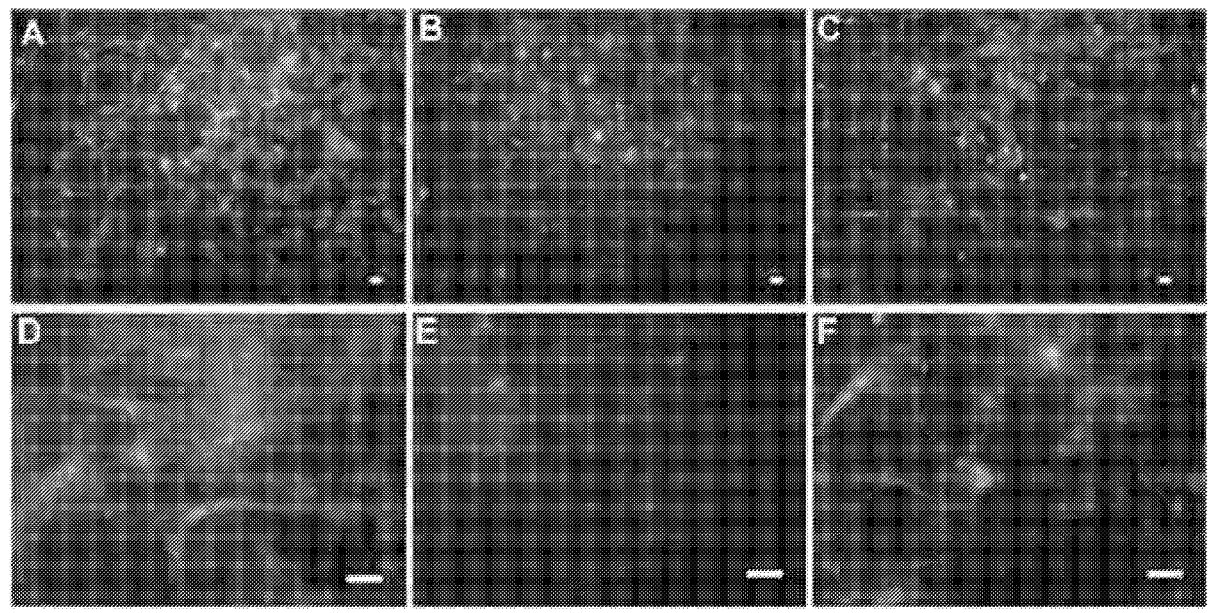
FIG. 6
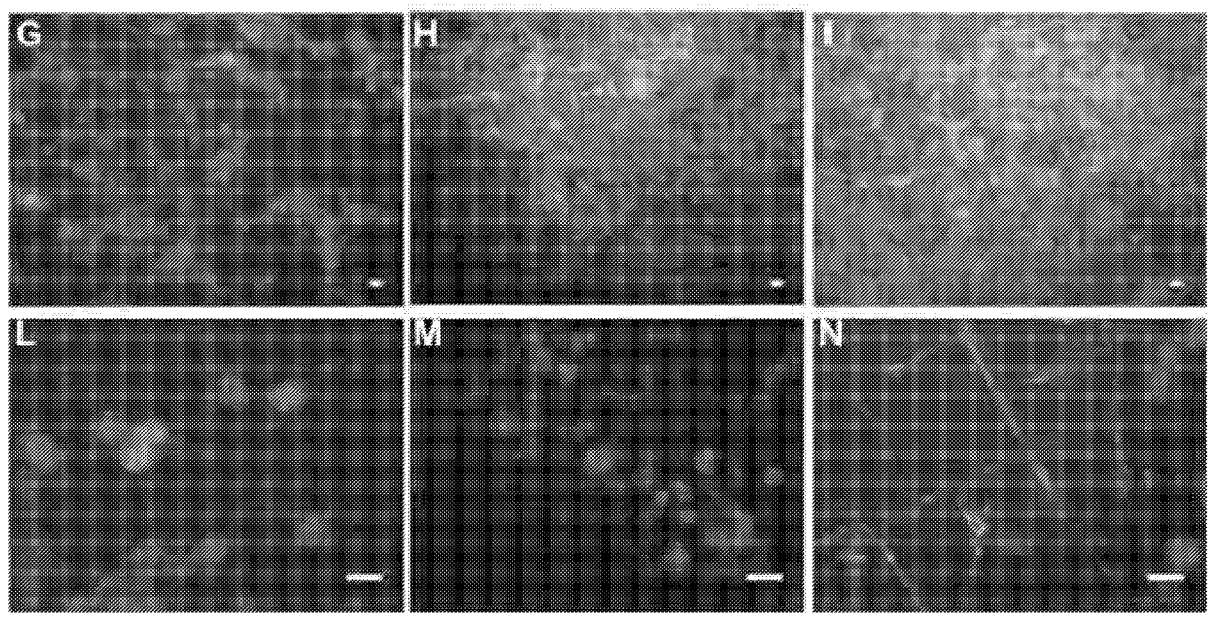

NANOPARTICLES OF CERIUM OXIDE TARGETED TO AN AMYLOID-BETA ANTIGEN OF ALZHEIMER'S DISEASE AND ASSOCIATED METHODS

RELATED APPLICATION

This application claims priority from copending provisional application Ser. No. 61/383,773, which was filed on 17 Sep. 2010, and which is incorporated herein by reference in its entirety.

STATEMENT OF GOVERNMENT RIGHTS

The invention claimed herein was made with at least partial support from the U.S. Government. Accordingly, the government may have certain rights in the invention, as specified by law.

FIELD OF THE INVENTION

The present invention relates to the field of neurological diseases and, more particularly, to a cerium oxide nanoparticulate composition useful in treatment of Alzheimer's disease.

BACKGROUND OF THE INVENTION

Current therapies for Alzheimer disease (AD) provide moderate symptomatic delay at various stages of the disease, but do not arrest the disease progression, and hence, new approaches to the disease management are urgently needed.

In recent years, cerium oxide nanoparticles have been studied as possible potent antioxidant agents that might be able to exert neuroprotective effects. We herein disclose the specific design of a targeted nanoceria-based formulation suitable for AD therapy. The test results obtained indicate the present composition is useful for selective delivery of immunonanoparticles to Aβ (amyloid-beta) plaques with concomitant rescue of neuronal survival and neurite dystrophy. The formulation appears to work by regulating the expression of the BDNF signal transduction pathway.

Oxidative stress and amyloid-beta (Aβ) are considered major etiological and pathological factors initiating and promoting neurodegeneration in Alzheimer's disease (AD) due to the production of free radicals (1-6). To date, use of multiple doses of antioxidants has met with onlyl limited success in abolishing these pathological conditions (7).

Recently, we have discovered that cerium oxide nanoparticles (CNPs) are redox active and biocompatible with both superoxide dismutase (8) and catalase mimetic activity (9). Among the lanthanide series of elements, cerium is distinctive in that it has two partially filled subshells of electrons, 4f and 5d, with many excited substates, resulting in a valence structure that undergoes significant alterations depending on the chemical environment (10-13). A predominant +3 oxidation state on the surface of CNPs is responsible for the nanoparticles' unique antioxidant properties (14, 15). We have shown that a single dose of CNPs prevents retinal degeneration induced by peroxides (16). In vitro, one low dose maintained radical scavenging and protective effects for long durations and multiple insults, suggesting the possibility of its regenerative activity. Therefore, CNPs have been investigated as possible nanopharmacological composition for use against diseases associated with oxidative stress (17-22).

Previously, on an AD human in vitro model, we have confirmed the anti-oxidant properties of CNPs. We have also demonstrated that CNPs do not act as mere anti-oxidant agents, but that they seem regulate signal transduction pathways involved in neuroprotection (23) To date, no early biomarkers for AD have been identified, therefore the appearance of symptoms is indicative of the full-blown disease.

The present disclosure concerns a novel approach wherein a CNP formulation comprises specifically targeted nanoparticles able to direct only to such targets as the brain areas of neurodegeneration and to exert specific effects counteracting neurite dystrophy and inhibiting disease progression. The presently disclosed composition is active at significantly lower dosages and in a single administration as opposed to free nanoparticles. This improvement was achieved by the synthesis of CNPs through the development of an improved method for the conjugation of anti-amyloid β antibodies to the nanoparticles with selective delivery to Aβ plaques and a concomitant increase of neuronal survival.

SUMMARY OF THE INVENTION

With the foregoing in mind, the present invention advantageously provides a composition of polyethylene glycol (PEG) coated nanoparticles of Cerium oxide having an antibody bound thereto, the antibody being specific for an antigen associated with a predetermined disease condition. Preferably, the nanoparticles are amine functionalized prior to coating, so as to promote coating by the PEG. In a preferred embodiment of the invention, the antibody is specifically targeted against an amyloid-beta antigen associated with a neurodegenerative disease. The nanoparticles are approximately from 3-5 nm in size prior to coating with PEG. The composition may be contained in a manufactured medication biologically acceptable for administration to a patient exhibiting symptoms of the predetermined disease. Accordingly, a method of treatment for the predetermined disease condition includes administration of the composition to a patient in need thereof.

More specifically, the present invention provides for a composition specifically targeted to a neurodegenerative disease, said composition comprising amine functionalized nanoparticles of Cerium oxide coated with polyethylene glycol and bearing an antibody specific for an antigen associated with the neurodegenerative disease. As noted above, this composition may also be contained in a manufactured medication biologically acceptable for administration to a patient exhibiting symptoms of the neurodegenerative disease. Included in this preferred embodiment of the invention is a method of treatment for a neurodegenerative disease, the method comprising administering this variation of the composition to a patient in need thereof.

A more specific yet embodiment of the present invention includes a composition immunologically targeted to Alzheimer's disease (AD), the composition comprising amine functionalized nanoparticles of Cerium oxide coated with polyethylene glycol and bearing an antibody specific for an amyloid-beta antigen associated with AD. This composition may be contained in a manufactured medication biologically acceptable for administration to a patient suffering from AD. This particular embodiment also includes a method of treatment for Alzheimer's disease, the method comprising administering the composition to a patient suffering from AD.

BRIEF DESCRIPTION OF THE DRAWINGS

Some of the features, advantages, and benefits of the present invention having been stated, others will become apparent as the description proceeds when taken in conjunction with the accompanying drawings, presented for solely for exemplary purposes and not with intent to limit the invention thereto, and in which:

FIG. 6 The upper panels show immunofluorescence analysis for NF-H 200 in control (A, D), Aβ-treated (B, E) cells and Aβ-CNP-Ab (C, F) treated cells. D, E, and F are higher magnification pictures. Bar=17 μm. Nuclei were stained with DAPI. Panels below show immunofluorescence analysis for GAP43 in control (G, L), Aβ-treated (H, M) cells and Aβ-CNP-Ab (I, N) treated cells. L, M, and N are higher magnification pictures. Bar=17 μm. Nuclei were stained with DAPI.

DETAILED DESCRIPTION OF THE PREFERRED EMBODIMENT

Figure 1:
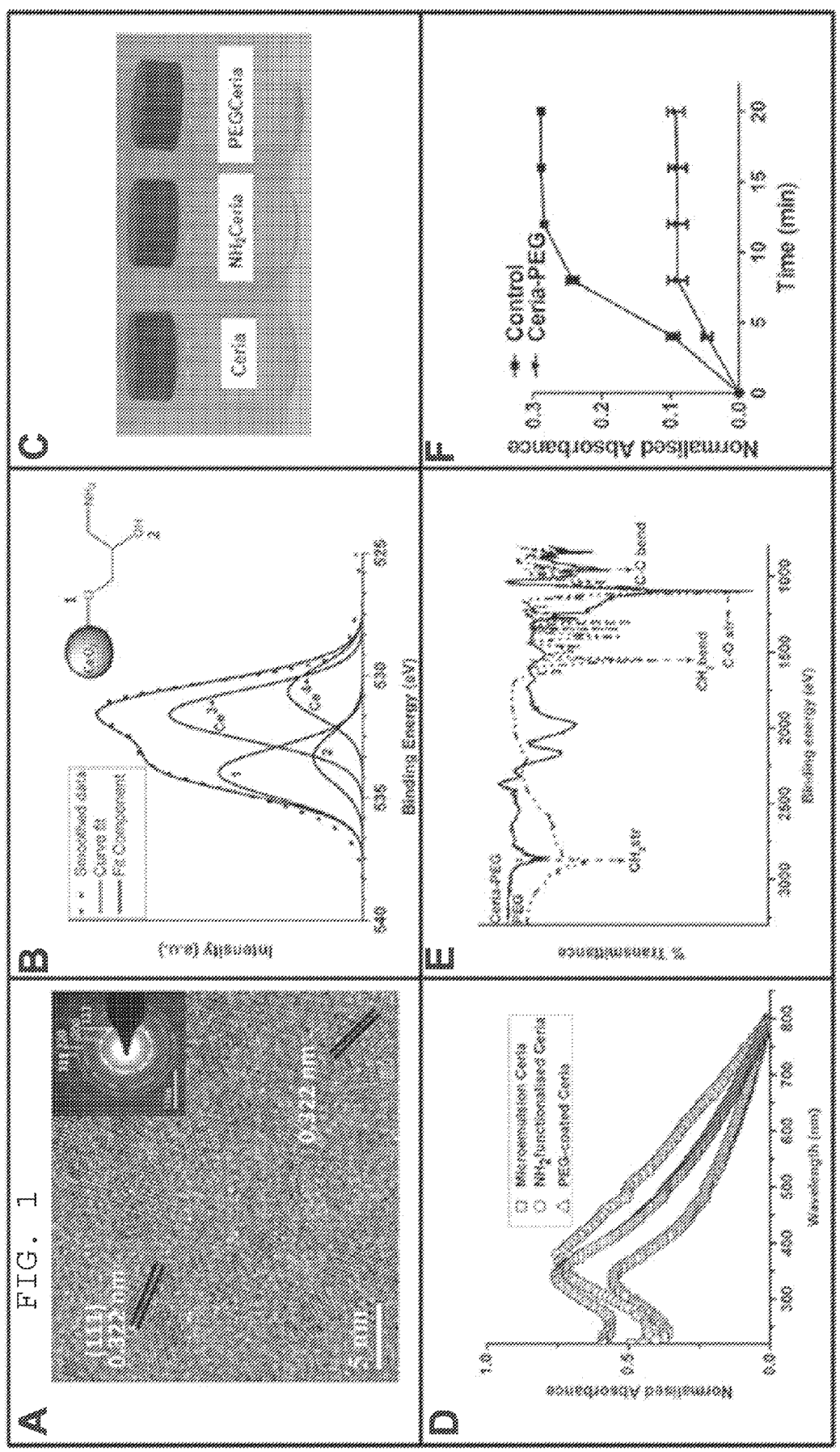
FIG. 1 presents the characterization of nanoceria: (A) HRTEM image of microemulsion nanoparticles showing control particle size distribution (3-5 nm) consistent to our group's well established synthesis procedure (42). The large d spaced planes (111) primarily easily focused at 300 kV is indicated in micrographs. Smaller d spacing planes (220,311) are not marked for clear representation of micrographs. The inset shows the selected area electron diffraction pattern of nanoparticle captured at low magnification confirming the crystalline nature and fluorite structure of CNPs by calculation of each diffraction ring diameter (Lλ=RD). (B) The amine functionalization of CNPs was confirmed by XPS. In the XPS two O (1s) peak corresponding two different valance state of ceria ($Ce^{3+}$ corresponds to 531.5 eV and $Ce^{4+}$ corresponds to 530.6 eV) and other two confirms the functionalization. Peak 1 is O—C bond that connects epichlorohydrin to the cerium oxide (534.00 eV) and peak 2 is epichlorohydrin's epoxy group (533.35 eV). (C) Shows change in the appearance of CNPs (yellow) after amine functionalization (light yellow) and PEG-conjugation (dark brown); (D) UV-VIS absorbance of ceria, $NH_2$-functionalized ceria and PEG coated CNPs, showing the shift in the absorbance maximum to red and blue shift after amine functionalization (38.45 nm) and PEG-conjugation (33.41 nm) (E) FTIR spectra of PEG conjugated cerium oxide nanoparticle confirming presence of PEG on CNPs; (F) SOD mimetic activity of PEG-CNPs as compared to control, showing that surface PEG-CNPs is still active and scavenges the radical efficiently.

The present invention will now be described more fully hereinafter with reference to the accompanying drawings, in which preferred embodiments of the invention are shown.

Unless otherwise defined, all technical and scientific terms used herein are intended to have the same meaning as commonly understood in the art to which this invention pertains and at the time of its filing. Although various methods and materials similar or equivalent to those described herein can be used in the practice or testing of the present invention, suitable methods and materials are described below. However, the skilled should understand that the methods and materials used and described are examples and may not be the only ones suitable for use in the invention.

Moreover, it should also be understood that any temperature, weight, volume, time interval, pH, salinity, molarity or molality, range, concentration and any other measurements, quantities or numerical expressions given herein are intended to be approximate and not exact or critical figures unless expressly stated to the contrary. Accordingly, where appropriate to the invention and as understood by those of skill in the art, it is proper to describe the various aspects of the invention using approximate or relative terms and terms of degree commonly employed in patent applications, such as: so dimensioned, about, approximately, substantially, essentially, consisting essentially of, comprising, and effective amount.

Further, any publications, patent applications, patents, and other references mentioned herein are incorporated by reference in their entirety as if they were part of this specification. However, in case of conflict, the present specification, including any definitions, will control. In addition, the materials, methods and examples given are illustrative in nature only and not intended to be limiting.

Accordingly, this invention may be embodied in many different forms and should not be construed as limited to the illustrated embodiments set forth herein. Rather, these illustrated embodiments are provided so that this disclosure will be thorough, complete, and will fully convey the scope of the invention to those skilled in the art. Other features and advantages of the invention will be apparent from the following detailed description, and from the claims.

Methods
Synthesis and characterization of CNPs CNPs of approximate size of 3-5 nm were synthesized by a microemulsion method describe elsewhere (36). After preparation, the particles were washed with acetone and water for six to eight times to remove the surfactant and other impurities. High resolution transmission electron microscopy (HRTEM), with FEI Tecnai F30 having an energy dispersive X-ray (EDX) analyzer, was carried out to study the size and morphology of the nanoparticles.

Amine Functionalization of CNPs
Prepared CNPs were suspended in 0.1 M NaOH solution and stirred for 5 minutes. Five milliliters of distilled epichlorohydrin and 0.5 mL of 2 M NaOH were added and stirred at room temperature. The nanoparticles were then recovered by centrifugation and washed with water several times. Next, the nanoparticles were suspended in water and 30% ammonium hydroxide solution was added and stirred for several hours. Finally, the resulting amine functionalized nanoparticles were recovered by centrifugation, washed with water (three to four times), and dried (37).

A 5400 PHI ESCA (XPS) spectrometer was used to obtain XPS data to confirm the amine functionalization. The base pressure during XPS analysis was 10-10 Torr and Mg—Kα X-radiation (1253.6 eV) at a power of 350 watts was used.

Preparation of PEG-CNPs
Polyethylene glycol (PEG) spacers with carboxy and amine terminals and having a spacer arm of 18.1 Å were selected for the study. We chose bi-functional PEG, so that one end can connect to an amine functionalized nanoparticle and the other end to the antibody. The carboxy terminal of the bi-functionalized PEG molecule was coupled to the amine functionalized CNPs using EDC and Sulfo NHS coupling chemistry. 1 mg/ml $CA(PEG)_4$ was dissolved in 0.05M NaCl, pH 6 buffer. 2 mM EDC and 5 mM Sulfo-NHS were added to the $CA(PEG)_4$ solution and stirred at room temperature. Amine functionalized CNPs were resuspended in sodium phosphate buffer, added to the reaction mixture and stirred. The molar ratio of amine functionalized ceria:$CA(PEG)_4$ was 1:4, used for the reaction. PEG-CNPs were recovered by centrifugation, washed with water (three to four times), and dried. UV-Visible spectroscopy and Fourier transform infrared (FTIR) spectra were obtained to confirm the PEG molecule on the nanoparticle surface using PerkinElmer Lamda750S and PerkinElmer Spectrum, respectively. Superoxide dismutase (SOD) mimetic activity of the PEG-conjugated CNP was estimated using SOD Assay kit (Sigma-Aldrich Corp., St. Louis, Mo., USA) according to the manufacturer instructions.

Conjugation of Aβ Antibody with PEG-CNP
In the first step, sodium azide and other salt were removed from the anti Aβ antibody by centrifuging through 10 kD cut-off Centricon® (Millipore Inc.). The antibody (1 mg/ml concentration) was diluted in NaCl, pH 6 buffer. 2 mM EDC and 5 mM Sulfo-NHS were added to the antibody solution and stirred at room temperature. PEG-CNPs were resuspended in sodium phosphate buffer, added to the reaction mixture and stirred. The molar ratio of amine functionalized antibody to PEG-CNPs used for the reaction was about 1:5. PEG-ceria nanoparticles were recovered by centrifugation, washed with water (three to four times), and re-suspended in distilled water. The concentration of ceria after antibody conjugation was assayed by UV-Visible spectroscopy. Bradford assays were performed to confirm antibody conjugation to the PEG-ceria nanoparticle.

Cell Cultures
SH-SY5Y cells (ATCC) were seeded at about $1\times10^4$ cells/$cm^2$ and cultured for 7 divisions (DIV) in FBS-free RPMI 1640 differentiating medium containing N2 supplement in order to promote neuronal differentiation.

Aβ Fibril Formation
Aβ(25-35) is frequently used in investigating Aβ properties as a less expensive and more easily handled substitute for the native full-length peptide, Aβ(1-42). Indeed, Aβ(25-35) mimics the toxicological and aggregation properties of the full-length peptide, though these characteristics are enhanced; i.e., the shorter peptide is more toxic to cultured neurons, exhibits earlier toxicity, causes more severe membrane protein oxidation, and aggregates faster than the native Aβ(1-42) (38).

The amyloid fibrils were obtained as previously described (39). Specifically, the Aβ(25-35) stock solution (500 μM) was prepared dissolving Aβ in FBS-free differentiating medium containing N2 supplement (pH 7.4) and stored at −20 C.°. The amyloid fibrils were obtained incubating Aβ(25-35) stock solution at 37° C. for 8 days.

Fluorimetric Assay

The amyloid polymerization status was checked by the thioflavin T (ThT) fluorescence method before each treatment (40). ThT binds specifically to amyloid fibrils, and such binding produces a shift in its emission spectrum and an increase in the fluorescent signal, which is proportional to the amount of amyloid formed (41-43). Following incubation, Aβ in 20 mM Tris HCl Buffer, pH 8.0, and 1.5 μM ThT in a final volume of 2 ml were analyzed. Fluorescence was monitored by spectrofluorimetry at an excitation wavelength of 450 nm and an emission wavelength of 485 nm, as previously described (41).

Treatments

Differentiated cells were treated with Aβ25-35 (12.5 μM, f.c.) for 24 h. For nanoparticles treatment, cells were subjected for 4 h to acute challenge with Aβ25-35, and were treated with an effective dose (200 nM, f.c.) of cerium oxide nanoparticles conjugated to anti-Aβ antibody (CNPs-Ab).

Aβ Plaque Detection

In order to asses if the ligation of antibody to the nanoparticles allows them to bind specifically to Aβ plaques, double immonoflorescence staining was performed. Briefly, cells, grown on coverslips, were fixed in 4% paraformaldehyde in PBS for 10 min at RT. Cells were then incubated with 0.05% solution of ThT and Tritc-labeled antirabbit IgG secondary antibody (1:100), for 20 min at RT. Nuclei were counterstained with DAPI (300 ng/ml). After extensive washings, coverslips were mounted with Vectashield mounting medium and photographed in a fluorescence microscope (AXIOPHOT, Zeiss).

Cell Viability and Death

Cells, plated in 24 multiwell plates, were incubated after treatments for 2 h with CellTiter 96 AQueous One Solution, a imetric viability test method based on 3-(4,5-dimethylthiazol-2-yl)-5-(3-carboxymethoxyphenil)-2-(4-sulfophenyl)-2H-tetrazolium (MTS). The quantity of formazan formed, as a function of viability, was measured at 490 nm using an ELISA plate reader. All MTS assays were performed in triplicate.

After Aβ exposure, cells on coverslips were fixed in 4% paraformaldehyde at room temperature for 10 min, then stained with DAPI (300 ng/ml) for 20 min and examined under UV illumination using a fluorescence microscope. To quantify the apoptotic process, nuclei with both fragmented or condensed DNA and normal DNA were counted. Five fields/coverslips were counted. Data, from 3 different experiments, are expressed as a percentage of the total cells counted. For apoptosis detection, cells were seeded in 24-well plates at a density of $1\times10^4$ cells/cm$^2$. Control and treated cells were analyzed for apoptosis using the cell death detection ELISA kit for the nucleosome detection. Absorbances at 405 nm with respect to 490 nm were recorded according to manufacturer's directions.

Morphometry

Control and treated cells, grown on coverslips, were fixed in 4% paraformaldehyde in PBS for 20 min at RT. After washings, coverslips were mounted with Vectashield® and phase-contrast observations were performed by an AXIO-PHOT Zeiss microscope, equipped with a micrometric ocular lens. The processes longer than the cell body mean diameter (Ø), which should be regarded as neurites, were counted and the results were expressed as neurite number vs. the total cell number. The neurite length was determined by comparing the neurite length with the mean diameter (Ø) of cell soma and reported as neurite length/soma (Ø).

Immunofluorescence

Control and treated cells, grown on coverslips, were fixed in 4% paraformaldehyde in PBS for 20 min at RT and permeabilized in PBS containing 0.1% Triton X-100 for 5 min at RT. Cells were then incubated with mouse anti-β-tubulin III (1:300) and anti PPARβ (1:100) diluted in PBS containing 3% BSA overnight at 4° C. The immunolocalization of GAP-43 and heavy neurofilament (NF-H) was performed by permeabilizing the fixed cells with absolute methanol for 10 min at −20° C. After that, cells were rehydrated with PBS for 5 min and incubated with anti-GAP 43 (1:300) and anti-NF-H, (1:200) antibodies, overnight at 4° C. After extensive washings with PBS, cells were treated with fluorescein-labeled anti-mouse or Tritc-labeled anti-rabbit IgG secondary antibodies (1:100 in PBS containing 3% BSA) for 30 min at RT. Nuclei were counterstained with DAPI (300 ng/ml). After extensive washings, coverslips were mounted with Vectashield mounting medium and photographed in a fluorescence microscope (AXIOPHOT, Zeiss).

Western Blot

Cells were washed in ice-cold PBS and homogenized in ice-cold RIPA buffer (10 mM Hepes, pH7.4, 10 mM KCl, 1.5 mM MgCl$_2$, 1 mM EDTA, 1 mM dithiothreitol) with a protease inhibitor mixture (100 mg/ml phenylmethylsulfonyl fluoride, 2 mg/ml aprotinin, 2 mM leupeptin, and 1 mg/ml pepstatin). The lysate was subjected to centrifugation at 600×g for 30 min at 4° C., and the supernatant was collected. Samples (25-50 μg/lane) were analyzed by 10% SDS-PAGE, transferred to PVDF membranes, and blocked in Tris-buffered saline containing 5% non fat milk, and 0.1% Tween20®. Membranes were incubated with different primary antibodies, anti-PPARβ (1:1000), anti-BDNF (1:200), anti TrkB (1:200) anti p-75 NTR (1:100), anti p-ERK1,2 (1:200), anti-ERK1,2 (1:1000), anti-p-ERK5 (1:200) overnight at 4° C. and then probed with horseradish peroxidase-conjugated mouse or rabbit secondary antibodies (1:1000). Immunoreactive bands were visualized by chemiluminescence. Band relative densities, against most evident band of PVDF membrane Comassie Blu stained, were determined using TotalLab® software (ABEL Science-Ware srl, Italy) and values were given as relative units.

Immunoprecipitation Assay

The immunoprecipitation assay was performed to estimate the amount of brain-derived neurotrophic factor (BDNF) protein in the culture media obtained from control and treated cells. To immunoprecipitate BDNF, a solution of 100 μg Protein A Sepharose A CL-4B was added to an equal amount (1000 μg of total protein) of supernatant samples collected from each condition. The suspension obtained was allowed to shake for 2 h at 4° C. and incubated with 5 μg of anti-BDNF primary antibody overnight at 4° C. The immunoprecipitates were then collected by centrifugation and the supernatant aspirated and discarded. Resuspended pellets were subjected to 15% SDS-PAGE, transferred to PVDF membranes and probed with specific anti BDNF antibody. After incubation with horseradish peroxidase-conjugated rabbit secondary antibodies (1:1000), the immunoreactive bands were visualized by chemiluminescence. Band relative densities were determined using TotalLab® software (ABEL Science-Ware srl, Italy) and values were given as percentage over control.

Statistics

Experiments were performed at least in triplicate. Data were represented as means±Standard Errors. Where appropriate, one-way ANOVA test followed by Scheffe's post hoc test analysis was performed using SPSS software. P values less than 0.05 were considered statistically significant.

Results

Functionalization and Characterization of CNPs

FIG. 1 shows the characterization of synthesized CNPs. In FIG. 1(A) depicts a TEM image showing well dispersed nanoparticle with a size distribution ranging approximately between 3-5 nm, (inset: X-ray diffraction pattern). The diffraction pattern showed typical peak broadening indicative of nanocrystalline particles (Suppl materials, Figure S1). X-ray spectroscopy illustrates the elemental composition which confirms that CNPs are free from any impurities (Suppl materials, Figure S2). FIG. 1B represents the high resolution XPS spectra of amine functionalized CNP, showing the evidence of complex formation. Peak 1 shows an O—C bond and represents the epichlorohydrin molecule attachment to the nanoparticle (534.00 eV) and peak 2 corresponds to epichlorohydrin's epoxy group (533.35 eV). The other two peaks are due to the presence of mixed valence state of cerium atom ($Ce+3$: 531.5 eV, $Ce+4$: 530.6 eV). FIG. 1C shows the change in the color of CNPs (dark yellow) after amine functionalization (light yellow) and PEG-conjugation (brown). Panel D presents the UV-Visible spectroscopy data showing a shift in the absorption spectrum of CNP following functionalization with NH2 (38.45 nm) and PEG (33.41 nm). The FTIR spectra (Panel E) of PEG-CNP, confirming the PEG conjugation; SOD mimetic activity of PEG coated CNP is presented in Panel F.

The conjugation of Anti-β-amyloid antibody with NH2 terminal PEG CNP is illustrated in scheme (Suppl materials Fig S3). The anti Aβ antibody was attached to the PEG-CNP using EDC/Sulfo NHS coupling reaction; the table shows the amount of antibody (μg/ml) in 5 mM PEG-CNP and CNP-NH2 estimated by Bradford assay.

Single Molecular Force Spectroscopy of CNPs

Figure 2:
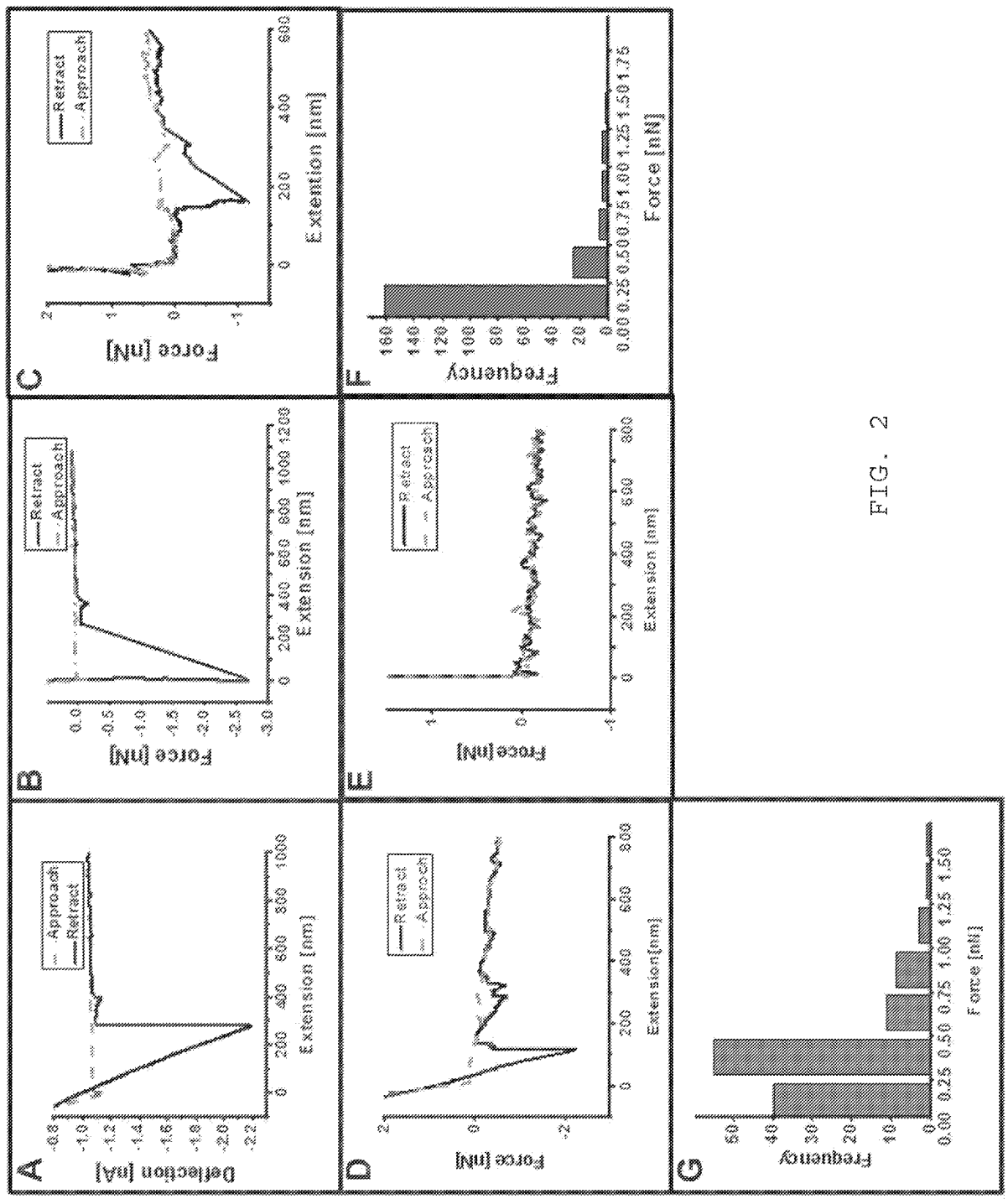
FIG. 2: SMFS measurements of Aβ-protein with bare CNP in aqueous medium; deflection-extension spectrum (A) and corresponding force-extension of Aβ with silicon substrate (B), interaction force of Aβ with bare ceria nanoparticle (C), amine functionalized CNPs (D), PEG-conjugated CNPs (E), Force histogram of Aβ with bare CNPs (F) and amine functionalized GNPs (G). Multiple SMFS were conducted for force and histogram on each sample. The total number of force and length values analyzed were n=204 (for F) and n=320 (for G).

We selected Aβ1-42 as a model protein to find out the interaction of the protein with bare and functionalized CNPs. FIG. 2 shows the single molecular force microscopy (SMFS) measurements carried out using a Succinimmide functionalized Silicone nitrite AFM tip (spring constant 0.01 N/m and tip radious of curvature 10 nm) coated with AF protein with bare CNPs. The figure shows the deflection-extension spectrum (A) and the corresponding force-extension (B) of Aβ with silicon. FIGS. (C), (D) and (E) show the interaction of Aβ with bare, NH2 and PEG functionalized CNPs, respectively. Attraction force of interaction was found in case of bare CNPs with the Aβ protein. The force histogram of Aβ with CNPs shows that the force of the interaction is in the range of 10-250pN (204 force curve analyzed) (F). The interaction force of Aβ is found to be higher with amine functionalized nanoparticles (2D) and force histogram shows (2G) that the amount of interaction is in the range of 250pN-500pN (320 force carve analyzed), greater than the bare CNPs, which indicates increased non specific interaction to the protein. Interestingly, minimum or no interaction has been observed with PEG-CNPs (2E). The interaction force is in the order: NH2-CNP>Bare CNP>PEG-CNP. This is explained in terms of zeta potential of the bare and functionalized nanoparticle. As the zeta potential is changed from positive to negative (NH2-CNP (+16 mV)<Bare CNPs (−10 mV)<PEG-CNP (−37 mV)), it minimizes the interaction with the partially negatively charged C-terminal part of the β-amyloid protein and the CNPs. Schematic diagram of CNP interaction with AFM probe functionalized with Aβprotein is consistent with our earlier studies dealing with tranferrin conjugated CNPs (24). It is noteworthy that the SMFM data suggested that PEG attachment with CNPs decreases the nonspecific interaction and its importance is discussed later.

CNPs-Ab Targeting Plaques

Figure 3:
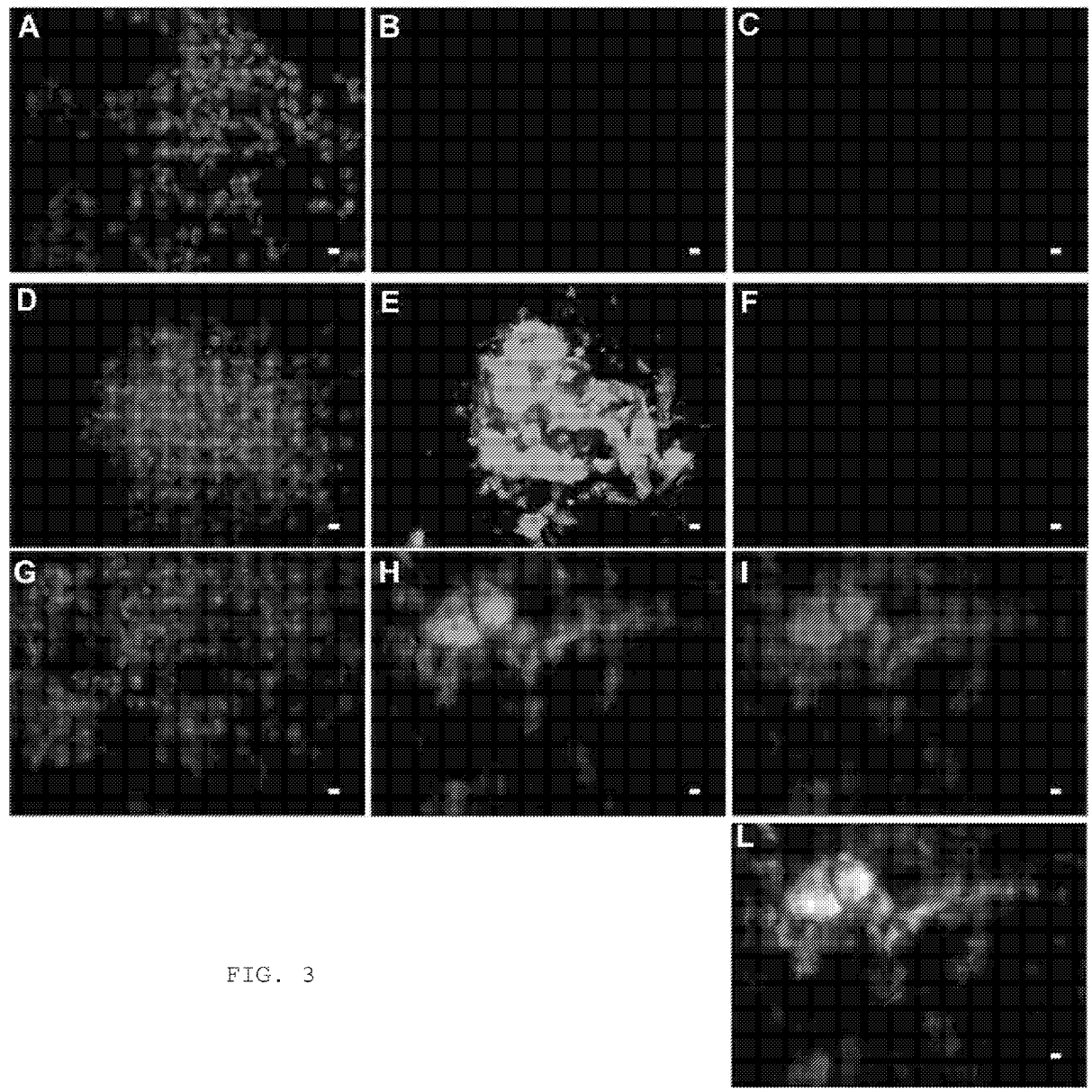
FIG. 3 Plaque presence is evaluated by ThT staining in control (B), Aβ treated (E) cells and Aβ-CNP-Ab (H). The ability of the conjugate to recognize the plaque is evaluated by TRITC labeled anti rabbit secondary antibody in control (C), Aβ-treated (F) cells and Aβ-CNP-Ab-treated cells (I). The ability of CNP-Ab to target only the plaque is shown in L, that is the merge of H and I. The nuclei are stained with DAPI in control (A), Aβ treated (D) cells and Aβ-CNP-Ab-treated cells (G). Bar=17 nm.

In FIG. 3 while control cells are negative to the thioflavine T staining (B), the green fluorescence shows the presence of Aβ plaque in Aβ-treated cells with (H) or without nanoparticles (E). The nuclei, stained with DAPI (D, G), show cell aggregation in the areas closed to the Aβ plaque, while control cells appear dispersed (A). In the same figure the ability of CNPs-Ab to bind the Aβ plaques is assessed by double immunostainining of thT and anti-rabbit Tritc-labeled secondary antibody (C, F, I L merge) which specifically recognizes the antibody bound to the nanoparticles. Tritc-antibody labels only cells treated with both Aβ plaque and CNP-Ab (I, L merge) not the control (C) and Aβ-treated (F) cells. Therefore, the ligation of the specific antibody against Aβ to the nanoparticles allows the CNPs-Ab to specifically recognize the plaque, having minimum or no interaction with nearby neuronal cells. This is supported by the effects observed when the same antibody used in the ligation is utilized alone to treat the cells after the Aβ challenge (Suppl materials, Fig. S4); in fact, it identifies the plaque (A, B, C) but having minimum or no effect on cell viability (D).

Cell Viability and Death

Figure 4:
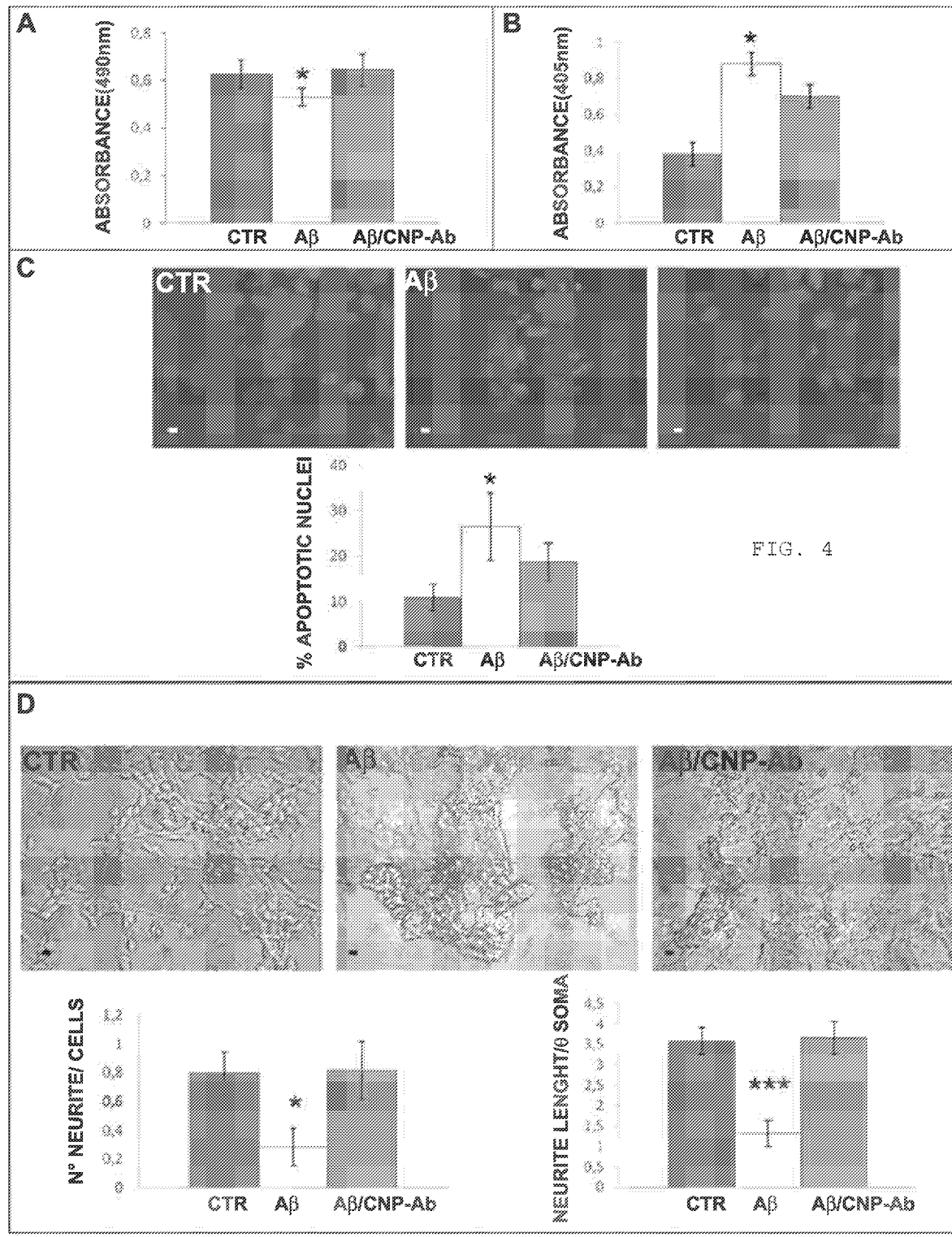
FIG. 4 Panel A shows cell viability evaluated by MTS assay, in control (CTR), Aβ treated (Aβ) cells and Aβ-CNP-Ab-treated cells. Data are means±SE, N=6, p=0.025, *p≤0.05; *, expressed vs control value. Panel B shows apoptotic cell death, evaluated as nucleosome concentration in control (CTR), Aβ treated (Aβ) cells and Aβ-CNP-Ab-treated cells. Data are means±SE, N=3, p=0.001, **p≤0.005*, expressed vs control value. Panel C shows cell death, evaluated by DAPI nuclear staining and by counting condensed nuclei in control, Aβ treated cells and Aβ-CNP-Ab-treated cells Data are means±SE, N=3, p=0.03, *p≤0.05; *, expressed vs control value. Bar=17 um. Panel D: Phase-contrast microscopy in control (CTR), Aβ treated (Aβ) cells and Aβ-CNP-Ab-treated cells. Bar 17 nm; On the left the neurite number in control, Aβ treated cells and Aβ-CNP-Ab treated cells is reported. Histograms report n°-neurites/n°-cells. Data are means±SE, N=3, p=0.024, *p≤0.05. On the right the neuritic length in control, Aβ treated cells and Aβ-CNP-Ab-treated cells. The neurite length was determined as neurite length/Ø soma. Data are means±SE, N=4, p=0.000, ***p≤0.0005. *, expressed vs control value.

Preliminary experiments (Suppl materials, Fig S5) the effects on cell viability of PEG-CNP or $NH_2$—CNP administered alone or after Aβ challenge indicated that PEG-CNP are more effective than $NH_2$—CNP in promoting neuronal survival due to the decrease in non-specific interaction in PEG CNP. CNPs-PEG-Ab were found to be more effective as compared to PEG-CNP. Therefore, in all subsequent experiments only the PEG-CNPs-Ab (CNPs-Ab) were used. Cell viability, evaluated by MTS assay, in control and treated cells is shown in FIG. 4, panel A. Aβ treatment leads to significant reduction in cell viability. CNPs-Ab revert this effect to the control values. In the same figure (panel B) apoptotic cell death, evaluated as nucleosome concentration, is shown. Aβ treatment induces a significant increase in apoptotic cell death, while after CNPs-Ab treatment no significant differences are observed with respect to the control. Panel C shows the nuclear fragmentation in control and treated cells, evaluated by DAPI nuclear staining. Consistently with the apoptotic assay, Aβ treatment leads to an increase in apoptotic nuclei, while CNPs-Ab almost restores the control condition. These results, taken together, indicate that the CNPs-Ab play a protective effect against the Aβ cytotoxic insult.

Cell Morphology

FIG. 4, panel D, shows the contrast phase microscopy and the graphic representation of neurite length and number in control and treated cells. Control cells (CTR) show an evident neuronal clustering and neuronal aggregation, Aβ treatment induced an evident neurite loss (Aβ). CNPs-Ab protects cells from neurite atrophy (Aβ-CNP-Ab). The graphical representation of number of neurite (left side), and of neurite length (right side) shows that Aβ treatment significantly decreases neurite number and also the neurite length, while CNPs-Ab protect the neurites from Aβ-mediated neuronal damage.

Immunofluorescence

Figure 5:
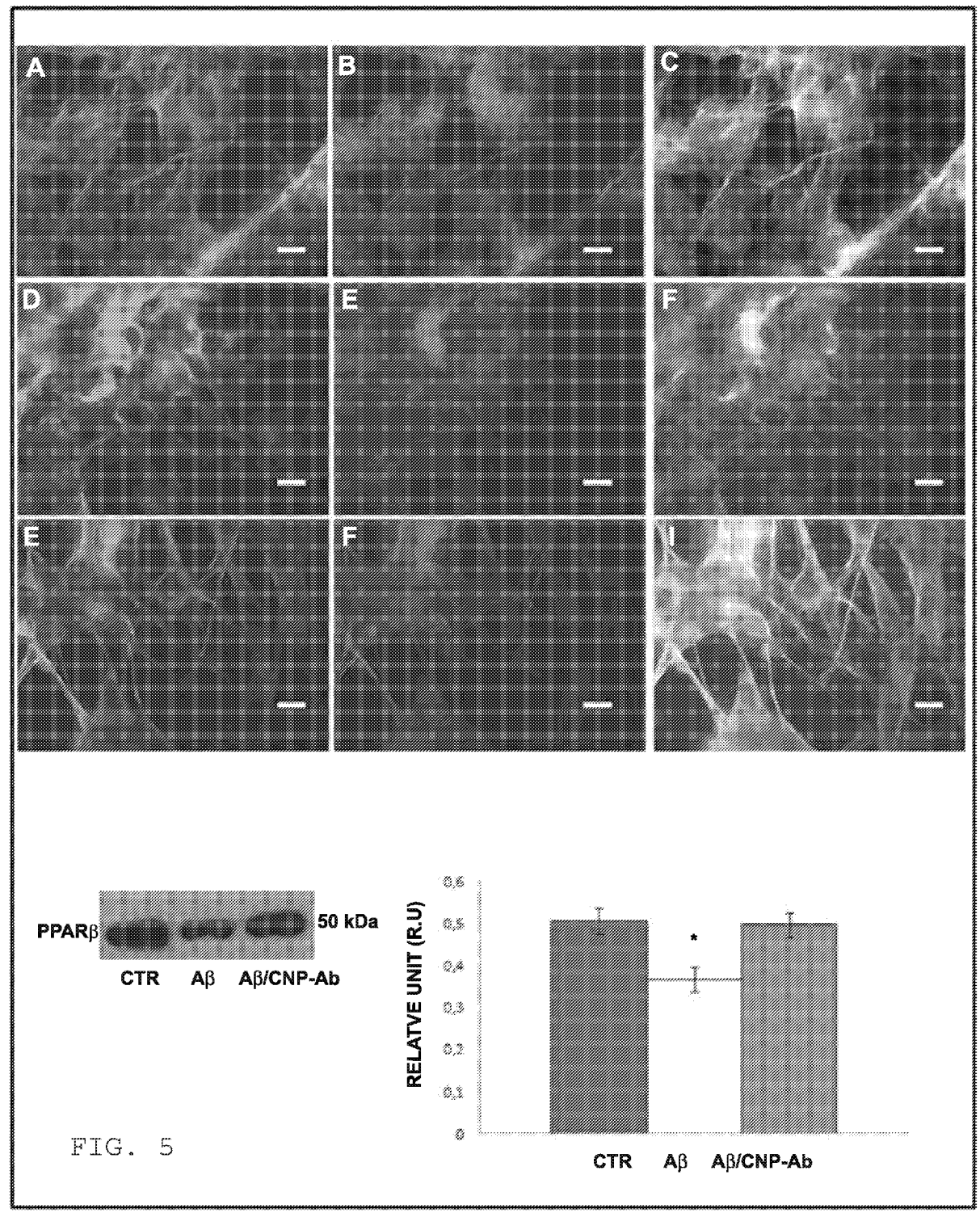
FIG. 5 Subcellular localization of the neuronal differentiation markers β-tubulin III (β-TubIII) (green) and PPARβ/δ (red) in control (A, B; C), Aβ-treated (D, E, F) cells and Aβ-CNP-Ab (G, H, I) treated cells. In C, F and I the merged images are shown. Bar=17 nm. In the bottom western blotting and densitometric analyses for PPARβ/δ in control (CTR), Aβ-treated (Aβ) cells and Aβ-CNP-Ab-treated cells. Band relative densities were determined against most evident band of PVDF membrane Comassie Blu stained. Data are means±SE, N=3, p=0.009, *p≤0.05. *, calculated vs control value.

Since we have previously demonstrated that Aβ treatment affected the expression of peroxisome proliferator activated receptor β (PPARβ), which is a transcription factor in neuronal differentiation (25), and in neuronal maturation (26-27), in the following experiments we analyzed the cytoskeletal organization and the PPARβ/δ expression and localization in control and treated cells. In FIG. 5, double immunostaining for 13-tubulin III, a marker of early neuronal differentiation and PPARβ/δ is shown. In control cells, β-tubulin III (CTR) localizes at cytoplasmatic and neurite level, while PPARβ/δ is mainly localized to the nuclei (CTR, merge). After Aβ treatment the neurite network is no more evident (Aβ) and the PPARβ/δ is mainly localized to the cytoplasm (Aβ merge).

In the β-treated cells following CNPs-Ab an evident preservation of neurite network (Aβ-CNP-Ab merge) as well as of the PPARβ/δ nuclear localization is observed (Aβ-CNP-Ab merge), thus indicating protection of neurites by nanoceria. Regarding PPARβ/δ protein levels, Aβ treatment significantly downregulates the protein, while CNPs-Ab revert PPARβ/δ protein levels to the control (FIG. 5 bottom).

In FIG. 6 the heavy neurofilament 200 (NF-H) and GAP-43 localization in control and treated cells is shown. NF-H is a marker of neuronal terminal maturation, while GAP-43 is an axonal marker. In control cells a wide neuronal network is observed (A and D, G and L), while in Aβ-treated cells the network is completely lost (B and E, H and M). After CNPs-Ab treatment an evident preservation of the neurites is observed (C and F, I and N), thus confirming the neuroprotective effects by the presently disclosed nanoceria composition in counteracting neuronal dystrophy.

Signal Transduction Pathways

Figure 7:
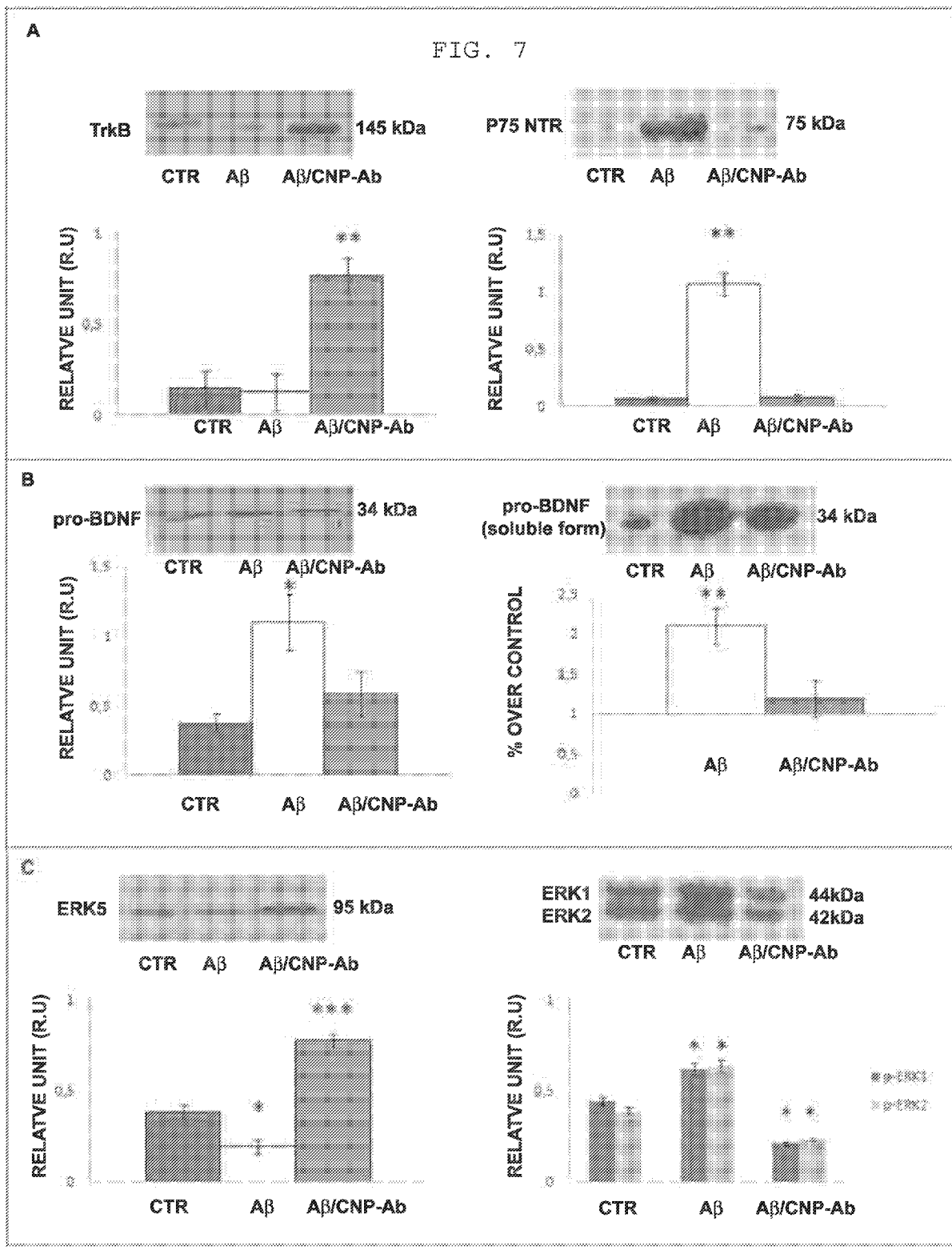
FIG. 7 Panel A shows western blotting and densitometric analyses for TrkB, P75NTR and cytoplasmatic pro-BDNF, in control (CTR), Aβ-treated (Aβ) cells and Aβ-CNP-Ab-treated cells Band relative densities, were determined against most evident band of PVDF membrane Comassie Blu stained. Data are means±SE, N=3, for TrkB p=0.04, *p≤0.05. For P75NTR p=0.004, p≤0.005; For pro-BDNF p=0.005, p≤0.005 The * is calculated vs control (CTR) value. Panel B shows western blotting and densitometric analyses for extracellular and soluble pro-BDNF form assayed by immunoprecipitating the culture media from control, Aβ-treated and Aβ-CNP-Ab-treated cells. The immunoprecipitation assay was performed allowing the collected media to be absorbed on Protein A Sepharose A CL-4B followed by a precipitation step with a specific anti-BDNF antibody Band relative densities were determined using TotalLab software (ABEL Science-Ware srl, Italy) and values were given as % over control. Data are means±SE, N=3, p=0.009, *p≤0.05* is calculated vs control value. Panel C shows western blotting and densitometric analyses for p-ERK1,2 and p-ERK5, in control, Aβ-treated cells and Aβ-CNP-Ab-treated cells. Band relative densities, were determined against most evident band of PVDF membrane Comassie Blu stained. Data are means±SE, N=3, for p-ERK1: Aβ vs CTR p=0.004, p≤0.005; Aβ-CNP-Ab vs CTR p=0.001, p≤0.005. For p-ERK2: Aβ vs CTR p=0.001, **p≤0.005. Aβ-CNP-Ab vs CTR p=0.016, *p≤0.05. For p-ERK5: Aβ vs CTR p=0.012, *p≤0.05; Aβ-CNP-Ab vs CTR p=0.000, ***p≤50.0005. * is calculated vs control value.
Figure 8:
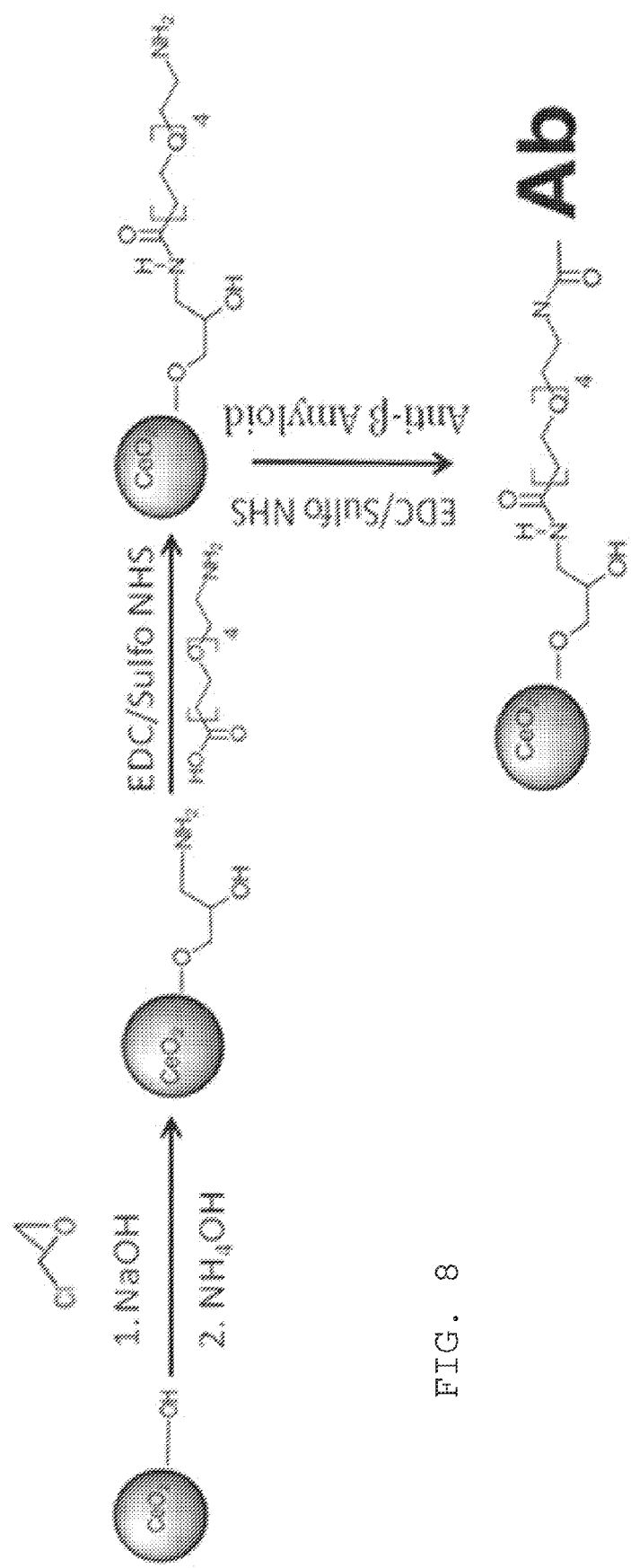
FIG. 8 shows the diffraction pattern of nanoceria showing typical peak broadening indicative of nanocrystalline particles.
Figure 9:
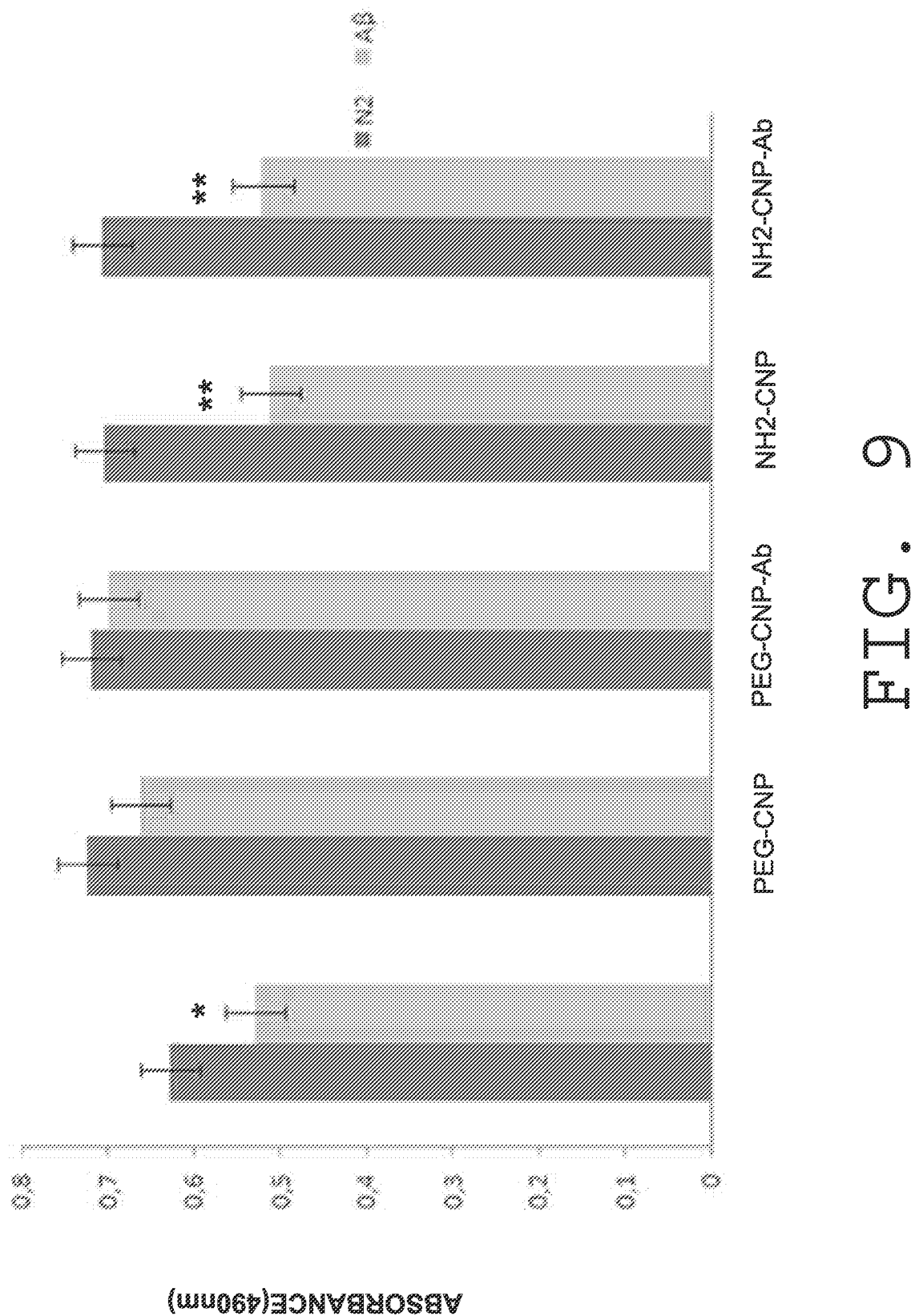
FIG. 9 depicts the results of Energy dispersive X-ray spectroscopy illustrating the elemental composition which confirms that CNPs are essentially free of impurities.
Figure 10:
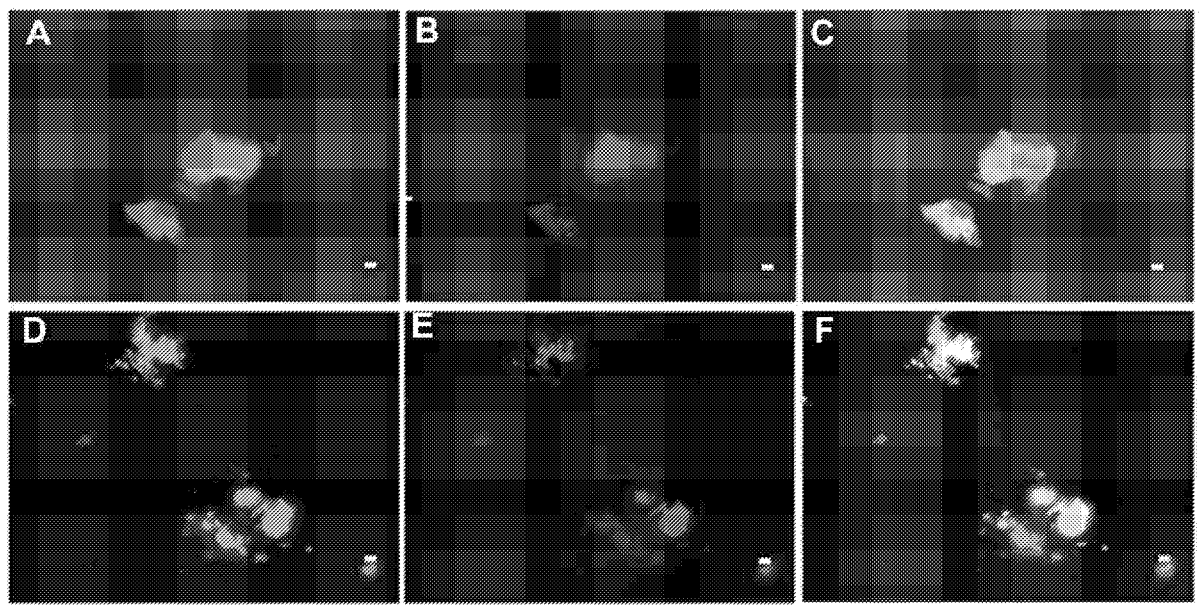
FIG. 10 portrays the conjugation of Anti-β-amyloid antibody with NH2 terminal PEG CNP.
Figure 10:
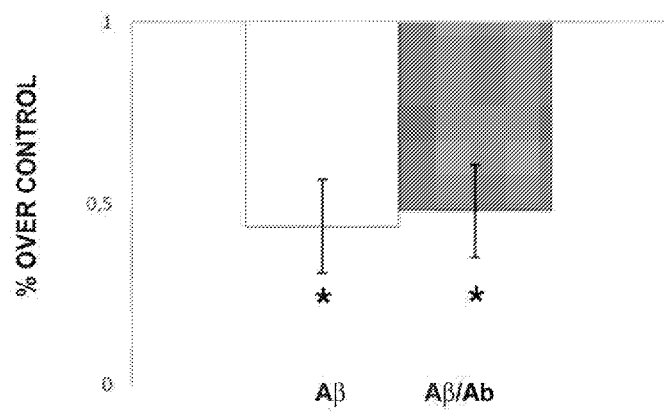
Figure 11:
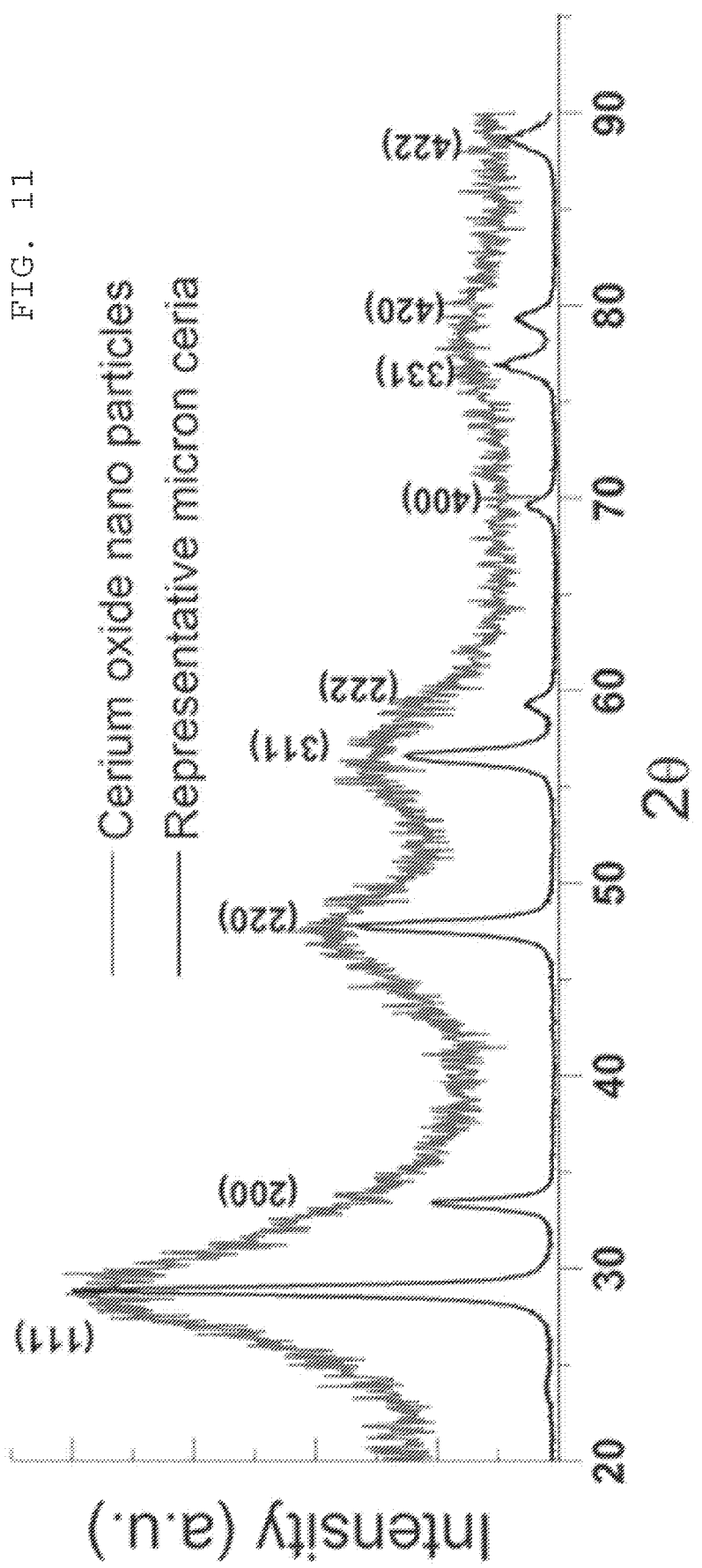
FIG. 11 shows the ligation of the specific antibody against Aβ to the nanoparticles allows the CNPs-Ab to specifically recognize the plaque, having minimum or no interaction with nearby neuronal cells. This notion is supported by the effects observed when the same antibody, utilized for the ligation, is utilized alone to treat the cells after the Aβ challenge; in fact, it identifies the plaque (A, B, C) but having minimum or no effect of cell viability (D).
Figure 12:
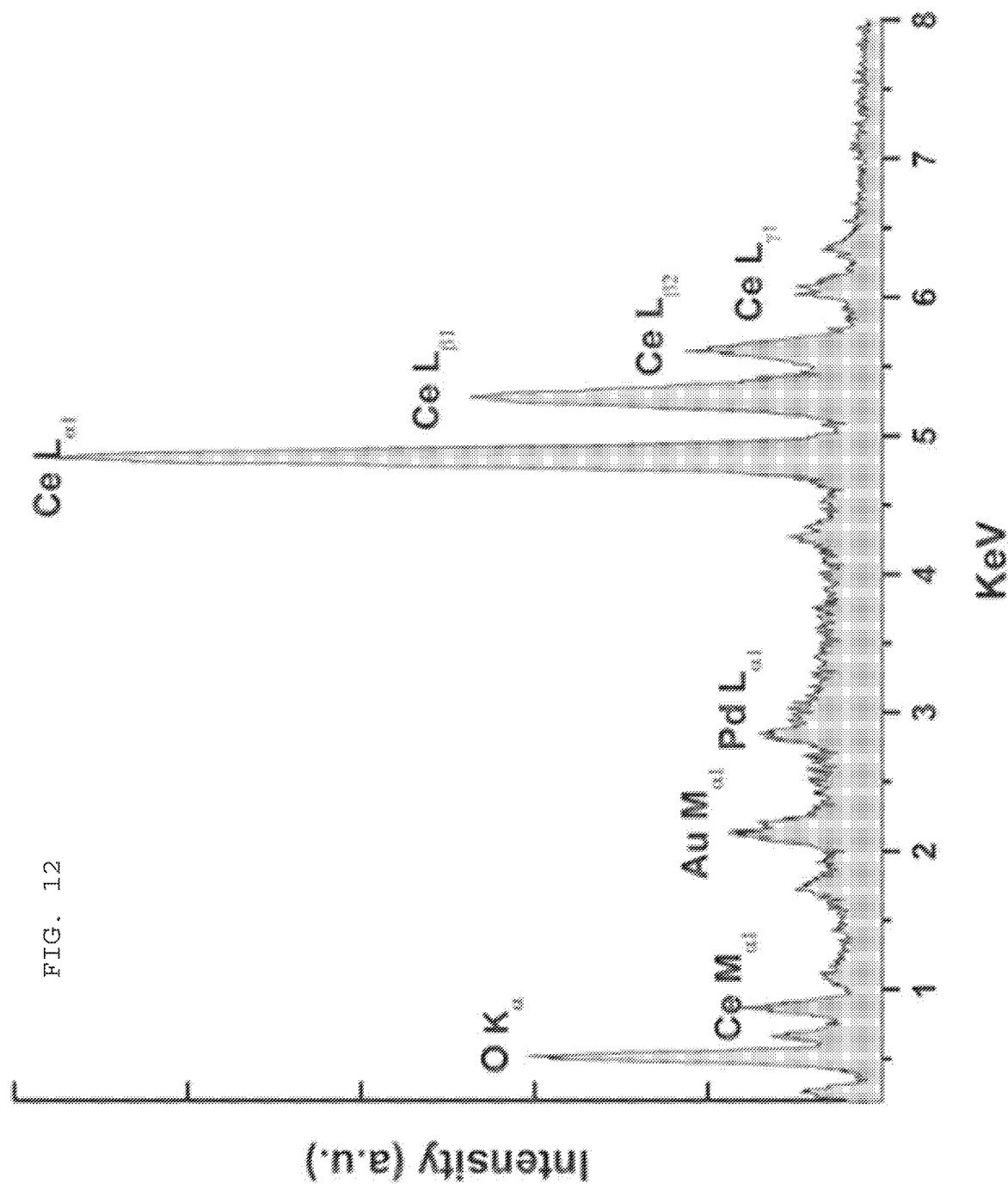
FIG. 12 presents preliminary experimental results showing the effects on cell viability of PEG-CNP or NH2-CNP administered alone or after A-beta challenge indicated that PEG-CNP are more effective than NH2-CNP in promoting neuronal survival. Nevertheless CNPs-PEG-Ab were found to be more effective as compared to PEG-CNP.

Finally, since neuronal morphology and plasticity are correlated to the brain derived neurotrophic factor (BDNF) signal transduction pathway, we assayed the BDNF, its receptors such as TrkB and p75, and the extracellular signal regulated kinases such as ERK1,2 and ERK5. Upon Aβ challenge, the cytoplasmatic levels of BDNF immature form (pro-BDNF) show to be upregulated (FIG. 7 panel B); The same results are obtained by the immunoprecipitation assay of the culture media (FIG. 7 panel B), indicating that Aβ injury leads to a strong accumulation of pro-BDNF in the extracellular matrix. This significant increase in pro-BDNF may be responsible for the promotion of the neuronal death and atrophy, as it is known that the immature form of BDNF induces neuronal apoptosis via activation of a receptor complex of p75NTR and sortilin (28). This view is supported by the results obtained for p75NTR protein in our experimental condition (FIG. 7 panel A). In fact, as for pro-BDNF, Aβ increases p75NTR protein levels while concomitantly triggering a decrease of the specific receptor TrkB involved in the action of mature and cleaved form of BDNF. Moreover Aβ induces the active form of ERK1,2 (p-ERK1,2) (FIG. 7 panel C), known to be involved in apoptosis promotion. In Aβ-treated cells following CNPs-Ab a reduction but not a complete reversion of pro-BDNF levels is observed, while the levels of the mature form are reverted to the control values. In the same time, CNPs-Ab, significantly increase TrkB as well as the p-ERK5, involved in neuronal survival, with concomitant decrease of ERK1,2, suggesting an activation of the neuronal survival pathway BDNF/TrkB/ERK5.

Discussion

It has been previously reported that GNPs protect neurons from free radical—mediated insult initiated by UV light, $H_2O_2$, irradiation, and excitotoxicity (29-30). Our previous results have documented the anti-oxidant and protective role of bare cerium oxide nanoparticle in a human AD in vitro model.

In this work we have carefully designed and formulated a targeted pegylated nanoceria-based molecule suitable as therapy for AD. Design of a specifically targeted nanoparticle avoids diffusion to other areas and in the cell cytoplasm. The conjugation of CNPs with an antibody against Aβ 1-42 makes possible a targeted delivery of CNPs to the Aβ plaques.

In this composite nanoparticle we have also used the 18.1 Å length bi-functional PEG as a spacer to conjugate anti Aβ antibody with amine functionalized CNPs. The SMFP data showed that the attachment of PEG to CNPs reduces non-specific interactions with Aβ proteins and protects the antioxidant properties of the CNPs while targeting the plaques. In the presently disclosed composition PEG acts as a spacer which also provides flexibility to the conjugated antibody to interact with its ligand with minimal steric hinderance.

Moreover, PEG coating will also provide the following advantages apart from the specific targeted delivery: (i) causing high disparity of nanoparticles; (ii) protecting nanoparticles from agglomerating and being cleared out from the system, (iii) minimizing the attachment of opsonin protein and suppressing uptake by macrophages, and (iv) increasing blood circulation time (31).

The immunofluorescence results obtained indicate the specific targeting of nanoceria to Aβ plaques without diffusion to the cell cytoplasm. It is noteworthy that the specific formulation now proposed is effective at a significantly lower concentration than bare CNPs which may decrease the potential drug side-effects. Moreover CNPs-Ab other than exerting non-specific antioxidant effects, seem to modulate at translational level proteins crucial for the neuronal signal transduction pathway leading to survival, such as TrkB and p-ERK5, which appeared significantly upregulated, and the proapoptotic signaling proteins such as BDNF/p75/p-ERK1,2, which appeared down-regulated. Consistently with the increase of the survival and plasticity pathways, the neuronal cytoskeleton, strongly damaged by Aβ challenge, appeared completely preserved in Aβ-treated cells in presence of CNPs-Ab.

Nanoparticles have been largely employed to deliver various types of drugs ranging from coenzyme Q10 (32), to protein antigens (33), plasmid DNA (34) and several other molecules. Specific nanoparticles were demonstrated to penetrate the blood-brain barrier (BBB) without altering its permeability and to be circulating in the blood for a long time (35). However, the inventive nanoceria composition disclosed herein demonstrates the use of functionalized self targeting nanoceria bound to a specific carrier for counteracting brain pathologies characterized by oxidative stress, and has shown to be effective in counteracting disease progression by improving neuronal viability while decreasing neuronal death and neurite atrophy.

Accordingly, in the drawings and specification there have been disclosed typical preferred embodiments of the invention and although specific terms may have been employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

REFERENCES

1. Harman D. The Free Radical Theory of Aging. Antioxid Redox Sign 2003; 5:557-561.

2. Halliwell B. Oxidative stress and neurodegeneration: where are we now? J Neurochem 2006; 97:1634-1658.

3. Howes R M. The Free Radical Fantasy. Ann New York Acad Scis, 2006; 1067:22-26.

4. Warner D S, Sheng H & Batinic-Haberle I. Oxidants, antioxidants and the ischemic brain. J Exp Biol, 2004; 207: 3221-3231.

5. Grune T. & Davies K. in In Handbook of the biology of aging Vol. 25. (. E. Masoro & S. Austad eds; Academic Press: San Diego, 2001.

6. Leker R R & Shohami, E. Cerebral ischemia and trauma—different etiologies yet similar mechanisms: neuroprotective opportunities. Brain Research Reviews 2002; 39:55-73.

7. Knott A B, Perkins G, Schwarzenbacher R & Bossy-Wetzel E. Mitochondrial fragmentation in neurodegeneration. Nat Rev Neurosci 2008; 9:505-518.

8. Korsvik C, Patil S, Seal S & Self W T. Superoxide dismutase mimetic properties exhibited by vacancy engineered ceria nanoparticles. Chemi Commun, 2007:1056-1058.

9. Pirmohamed T, Dowding J M, Singh S, Wasserman B, Heckert E, Karakoti A S, King J E Seal S Self W T Nanoceria exhibit redox state-dependent catalase mimetic activity. Chem Commun 2010; 46:2736-2738.

10. Aneggi E, Boaro M, Leitenburg C D, Dolcetti G & Trovarelli A. Insights into the redox properties of ceria-based oxides and their implications in catalysis. J Alloys and Compounds 2006; 408-412:1096-1102.

11. Trovarellis A. Catalysis by ceria and other related materials, Vol. 2. Imperial College Press: London, UK, 2002

12. Zhang F, Wang P, Koberstein J, Khalid S & Chan S W. Cerium oxidation state in ceria nanoparticles studied with X-ray photoelectron spectroscopy and absorption near edge spectroscopy. Surface Science 2004; 563:74-82.

13. Davis V T & Thompson J S. Measurement of the Electron Affinity of Cerium. Phys Rev Lett 2002; 88.073003.

14. Karakoti A, Singh S, Dowding J M Seal S & Self W T. Redox-active radical scavenging nanomaterials. Chem Soc Revs 2010; 39:4422-4432.

15. Heckert E G, Karakoti A S, Seal S & Self W T. The role of cerium redox state in the SOD mimetic activity of nanoceria. Biomaterials 2008; 29:2705-2709.

16. Chen J, Patil S, Seal S & McGinnis J F. Rare earth nanoparticles prevent retinal degeneration induced by intracellular peroxides. Nat Nano 2006; 1:142-150.

17. Celardo I, Traversa E & Ghibelli L. Cerium oxide nanoparticles: a promise for applications in therapy. J Exp Ther Oncol, 2011; 9:47-51.

18. Celardo I, Pedersen J Z, Traversa E & Ghibelli L. Pharmacological potential of cerium oxide nanoparticles. Nanoscale, 2011. [Epub ahead of print]

19. Hirst S M, Karakoti A S, Tyler R D, Sriranganathan N, Seal S, Reilly C M. Anti-inflammatory Properties of Cerium Oxide Nanoparticles. Small, 2009; 5:2848-2856.

20. Alili L, Sack M, Karakoti A S, Teuber S, Puschmann K, Hirst S M Brenneisen, P. Combined cytotoxic and anti-invasive properties of redox-active nanoparticles in tumor-stroma interactions. Biomaterials, 2011; 32:2918-2929.

21. Colon J, Hsieh N, Ferguson A, Kupeliani P, Seal S et al. Cerium oxide nanoparticles protect gastrointestinal epithelium from radiation-induced damage by reduction of reactive oxygen species and upregulation of superoxide dismutase 2. Nanomedicine-UK 2010; 6:698-705.

22. Varghese K, Das M, Bhargava N, Stancescu M, Molnar P, Kindy M S et al. Regeneration and characterization of adult mouse hippocampal neurons in a defined in vitro system. J Neurosci Meth, 2009; 177:51-59

23. D'Angelo B, Santucci S, Benedetti E, Di Loreto S, Phani R. A, Falone S et al. Cerium Oxide Nanoparticles Trigger Neuronal Survival in a Human Alzheimer Disease Model By Modulating BDNF Pathway. Curr Nanosci, 2009; 5:167-176.

24. Vincent A, Babu S. Heckert E, Dowding J, Hirst S M, Inerbaev T M et al. Protonated Nanoparticle Surface Governing Ligand Tethering and Cellular Targeting. ACS Nano 2009; 3:1203-1211

25. Di Loreto S, D'Angelo, B, D'Amico M, Benedetti E, Cristiano L, Cinque B et al. PPARβ agonists trigger neuronal differentiation in the human neuroblastoma cell line SH-SY5Y. J Cell Physiol 2007; 211:837-847 (2007).

26. D'Angelo B, Benedetti E. Di Loreto S, Cristiano L, Laurenti G, Cerù M. P et al. Signal transduction pathways involved in pparβ/δ-induced neuronal differentiation. J Cell Physiol, Epub ahead of print] (2010)

27. Cimini A. Benedetti E, Cristiano, L. Sebastiani P, D' Amico M A, D'Angelo B et al. Expression of peroxisome proliferator-activated receptors (PPARs) and retinoic acid receptors (RXRs) in rat cortical neurons. Neuroscience, 2005; 130:325-337

28. Teng H K, Teng K K, Lee R, Wright S, Tevar S, Almeida R D. et al. ProBDNF Induces Neuronal Apoptosis via Activation of a Receptor Complex of p75NTR and Sortilin. The Journal of Neuroscience, 2005; 25:5455-5463.

29. Das M. et al. Auto-catalytic ceria nanoparticles offer neuroprotection to adult rat spinal cord neurons. Biomaterials, 2007; 28:1918-1925.

30. Schubert D, Dargusch R, Raitano J & Chan S W Cerium and yttrium oxide nanoparticles are neuroprotective. Biochemical and Biophysical Research Communications, 2006; 342:86-91.

31. Karakoti A S, Das S, Thevuthasan S & Seal S. PEGylated Inorganic Nanoparticles. Angewandte Chemie International Edition, 2011; 50: 1980-1994.

32. Hsu C H, Cui Z, Mumper R J & Jay M. Preparation and Characterization of Novel Coenzyme Q10 Nanoparticle Engineered from Microemulsion Precursors AAPS PharmSciTech, 2003; 4:E32.

33. Cui Z & Mumper R. J. Topical immunization using nanoengineered genetic vaccines. Journal of Controlled Release, 2002; 81:173-184.

34. Cui Z & Mumper R. J. Genetic Immunization Using Nanoparticles Engineered from Microemulsion Precursors. Pharmaceutical Research, 2002; 19:939-946.

35. Lockman P R, Koziara J, Roder K E, Paulson J, Abbruscato T J, Mumper R J et al. Assessment of Baseline Blood-Brain Barrier Parameters in the Presence of Novel Nanoparticles. Pharmaceutical Research, 2003; 20:705-713.

36. Patil S, Kuiry S C, Seal S & Vanfleet R. Synthesis of Nanocrystalline Ceria Particles for High Temperature Oxidation Resistant Coating. Journal of Nanoparticle Research, 2002; 4:433-438.

37. Patil S, Reshetnikov S, Haldar M K, Seal S & Mallik S. Surface-Derivatized Nanoceria with Human Carbonic Anhydrase II Inhibitors and Fluorophores: A Potential Drug Delivery Device. J. Phys. Chem, 2007: 111:8437-8442.

38. Santos M J, Quintanilla R A, Toro A, Grandy R, Dinamarca M C, Godoy J A et al. Peroxisomal Proliferation Protects from β-Amyloid Neurodegeneration. Journal of Biological Chemistry, 2005; 280:41057-41068.

39. Varadarajan S, Kanski J, Aksenova M, Lauderback C & Butterfield D A. Different Mechanisms of Oxidative Stress and Neurotoxicity Alzheimer's A beta(1-42) and A beta(25-35). Journal of the American Chemical Society, 2001; 123: 5625-5631.

40. White J A, Manelli A M, Holmberg K H, Van Eldik L J & LaDu M J. Differential effects of oligomeric and fibrillar amyloid-[beta]1-42 on astrocyte-mediated inflammation. Neurobiology of Disease, 2005; 18:459-465.

41. Muñoz F J & Inestrosa N C. Neurotoxicity of acetylcholinesterase amyloid betapeptide aggregates is dependent on the type of Abeta peptide and the AChE concentration present in the complexes. FEBS Letters, 1999; 450:205-209.

42. Naiki H, Higuchi K, Nakakuki K & Takeda T. Kinetic analysis of amyloid fibril polymerization in vitro. Lab Invest 1991; 65:104-110.

43. Inestrosa N C, Alvarez A, Perez C A., Moreno R D, Vicente M, Linker C. et al Acetylcholinesterase Accelerates Assembly of Amyloid-[beta]-Peptides into Alzheimer's Fibrils: Possible Role of the Peripheral Site of the Enzyme. Neuron, 1996; 16:881-891.

That which is claimed:

1. A composition comprising polyethylene glycol (PEG) coated nanoparticles of Cerium oxide having an antibody bound thereto, the antibody being specific for an antigen associated with a predetermined disease condition, wherein the PEG comprises a bifunctional molecule comprising a carboxy terminal and amine terminal, the carboxy terminal being connected to an amine group on the nanoparticles and an amine terminal being connected to the antibody as follows:

$CeO_2$—NHCO—$[CH_2CH_2O]_n$—$CH_2CH_2NH$-antibody.

2. The composition of claim 1, wherein said nanoparticles are amine functionalized to promote coating by the PEG.

3. The composition of claim 1, wherein said antibody is specifically targeted against an amyloid-beta antigen associated with a neurodegenerative disease.

4. The composition of claim 1, wherein the nanoparticles are approximately from 3-5 nm in size prior to coating with PEG.

5. The composition of claim 1, contained in a manufactured medication biologically acceptable for administration to a patient exhibiting symptoms of the predetermined disease.

6. A composition specifically targeted to a neurodegenerative disease, said composition comprising amine functionalized nanoparticles of Cerium oxide coated with polyethylene glycol and bearing an antibody specific for an antigen associated with the neurodegenerative disease; wherein the PEG comprises a bifunctional molecule comprising a carboxy terminal and amine terminal, the carboxy terminal being connected to an amine group on the nanoparticles and an amine terminal being connected to the antibody as follows:

$CeO_2$—NHCO—$[CH_2CH_2O]_n$—$CH_2CH_2NH$-antibody.

7. The composition of claim 6, contained in a manufactured medication biologically acceptable for administration to a patient exhibiting symptoms of the neurodegenerative disease.

8. A method of treatment for a neurodegenerative disease, the method comprising administering the composition of claim 6 to a patient in need thereof.

9. A composition immunologically targeted to Alzheimer's disease (AD), said composition comprising amine functionalized nanoparticles of Cerium oxide coated with polyethylene glycol and bearing an antibody specific for an amyloid-beta antigen associated with AD, wherein the PEG comprises a bifunctional molecule comprising a carboxy terminal and amine terminal, the carboxy terminal being connected to an amine group on the nanoparticles and an amine terminal being connected to the antibody as follows:

$CeO_2$—NHCO—$[CH_2CH_2O]_n$—$CH_2CH_2NH$-antibody.

10. The composition of claim 9, contained in a manufactured medication biologically acceptable for administration to a patient suffering from AD.

11. A method of treatment for Alzheimer's disease, the method comprising administering the composition of claim 9 to a patient suffering from AD.

\* \* \* \* \*